United States Patent
Yerich et al.

(10) Patent No.: US 6,421,564 B1
(45) Date of Patent: Jul. 16, 2002

(54) BI-CHAMBER CARDIAC PACING SYSTEM EMPLOYING UNIPOLAR LEFT HEART CHAMBER LEAD IN COMBINATION WITH BIPOLAR RIGHT CHAMBER LEAD

(75) Inventors: Charles A. Yerich, Shoreview; Jean E. Hudson, Coon Rapids; Brian A. Blow, Maple Grove, all of MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/439,565

(22) Filed: Nov. 12, 1999

(51) Int. Cl.[7] .................................................. A61N 1/18

(52) U.S. Cl. ............................................................ 607/9

(58) Field of Search ............................... 600/374, 509; 607/4, 9

(56) References Cited

U.S. PATENT DOCUMENTS

| | | | |
|---|---|---|---|
| 3,937,226 A | 2/1976 | Funke | 128/419 PG |
| 4,088,140 A | 5/1978 | Rockland et al. | 128/419 PG |
| 4,332,259 A | 6/1982 | McCorkle, Jr. | 128/786 |
| 4,354,497 A | 10/1982 | Kahn | 128/419 D |
| 4,458,677 A | 7/1984 | McCorkle, Jr. | 128/786 |

(List continued on next page.)

FOREIGN PATENT DOCUMENTS

| | | | |
|---|---|---|---|
| DE | 196 15 159 | 10/1997 | A61N/1/362 |
| WO | WO 99/29368 | 6/1999 | A61N/1/37 |

OTHER PUBLICATIONS

Daubert et al., "Permanent Left Ventricular Pacing With Transvenous Leads Inserted Into The Coronary Veins", PACE (vol. 21, Part II, pp. 239–245, Jan. 1998).

Cazeau et al., "Four Chamber Pacing in Dilated Cardiomyopathy", PACE (vol. 17, Part II, pp. 1974–1979, Nov. 1994).

Daubert et al., "Renewal of Permanent Left Atrial Pacing via the Coronary Sinus", PACE (vol. 15, Part II, NASPE Abstract 255, p. 572, Apr. 1992).

Daubert et al., "Permanent Dual Atrium Pacing in Major Intra–atrial Conduction Blocks: A Four Years Experience", PACE (vol. 16, Part II, NASPE Abstract 141, p. 885, Apr. 1993).

Primary Examiner—Jeffrey R. Jastrzab
Assistant Examiner—Frances P. Oropeza
(74) Attorney, Agent, or Firm—Girma Wolde-Michael

(57) ABSTRACT

In a bi-ventricular pacing system, an implantable pulse generator optionally having an IPG indifferent electrode is coupled to a small diameter, unipolar, left ventricular (LV) lead and a bipolar right ventricular (RV) lead. The LV lead is advanced through the superior vena cava, the right atrium, the ostium of the coronary sinus (CS), the CS, and into a coronary vein descending from the CS to locate the LV active pace/sense electrode at a desired LV pace/sense site. An LV lead placed on an epicardial surface can substitute. The RV lead in a preferred embodiment is advanced into the RV chamber to locate RV active and indifferent pace/sense electrodes therein. Sensing of RV spontaneous cardiac depolarizations to provide a RV sense event signal and delivery of RV pacing pulses is conducted across the RV active pace/sense electrode and one of the RV or IPG indifferent pace/sense electrodes. Sensing of LV spontaneous cardiac depolarizations to provide a LV sense event signal is conducted across the LV active pace/sense electrode and one of the RV active or indifferent pace/sense electrodes or the IPG indifferent pace/sense electrodes. Delivery of LV pacing pulses is conducted across the LV active pace/sense electrode and the RV indifferent pace/sense electrode. A similar arrangement is disclosed for left atrial (LA) and right atrial (RA) pacing and sensing.

23 Claims, 8 Drawing Sheets

U.S. PATENT DOCUMENTS

| | | |
|---|---|---|
| 4,548,203 A | 10/1985 | Tacker, Jr. et al. ........ 128/419 D |
| 4,928,688 A | 5/1990 | Mower ................. 128/419 PG |
| 5,123,412 A | 6/1992 | Betzold ........................ 607/17 |
| 5,174,289 A | 12/1992 | Cohen ................. 128/419 PG |
| 5,267,560 A | 12/1993 | Cohen ........................ 607/25 |
| 5,387,228 A | 2/1995 | Shelton ....................... 607/11 |
| 5,403,356 A | 4/1995 | Hill et al. .................... 607/14 |
| 5,514,161 A | 5/1996 | Limousin ...................... 607/9 |
| 5,540,727 A | 7/1996 | Tockman et al. ............. 607/18 |
| 5,584,867 A | 12/1996 | Limousin et al. .............. 607/9 |
| 5,674,259 A | 10/1997 | Gray ........................... 607/20 |
| 5,720,768 A * | 2/1998 | Verboven-Nelissen ......... 607/9 |
| 5,728,140 A | 3/1998 | Salo et al. ..................... 607/9 |
| 5,741,309 A | 4/1998 | Maares ......................... 607/9 |
| 5,792,203 A | 8/1998 | Schroeppel .................. 607/30 |
| 5,797,970 A * | 8/1998 | Pouvreau ...................... 607/9 |
| 5,902,324 A | 5/1999 | Thompson et al. ............. 607/9 |

* cited by examiner

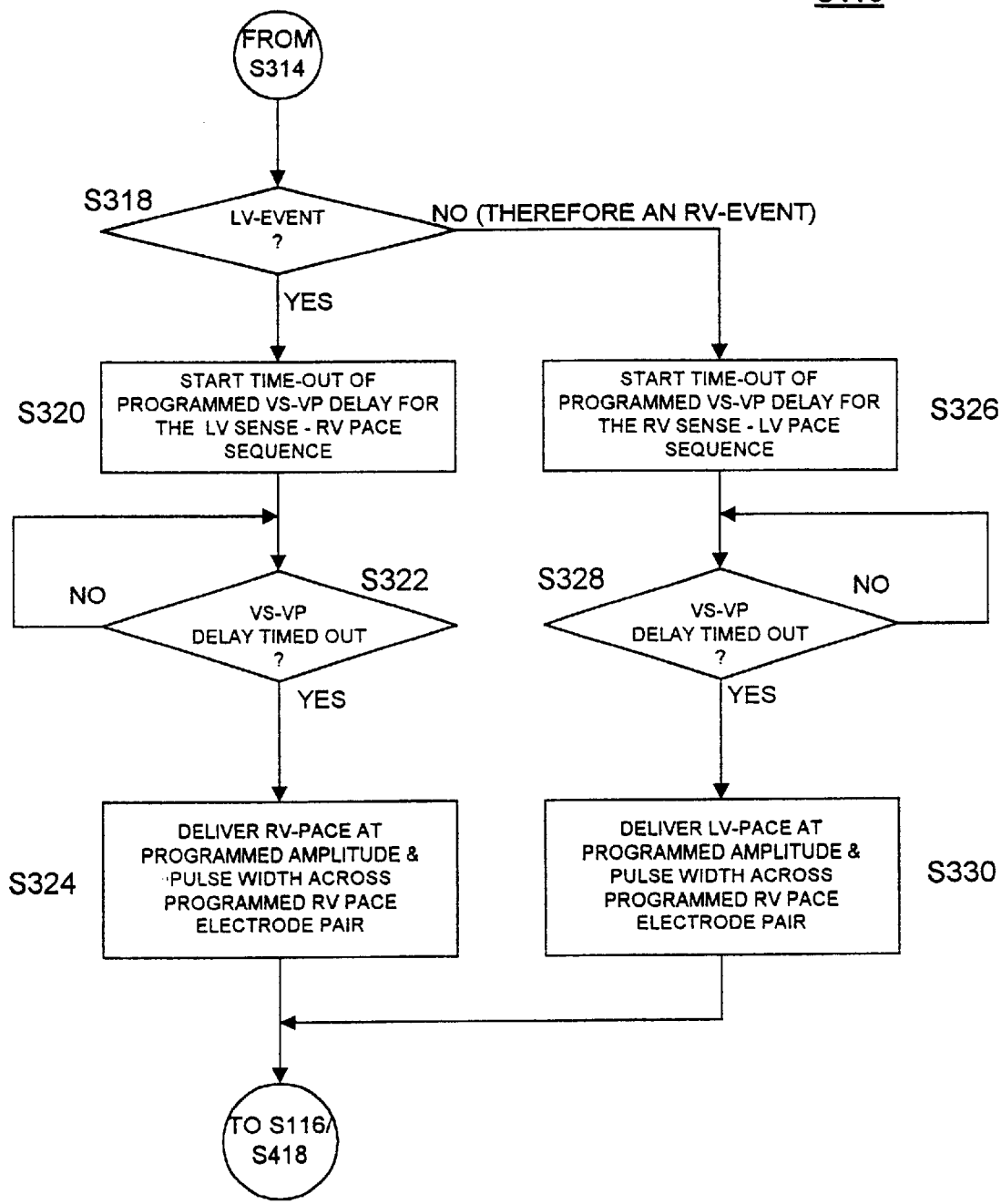

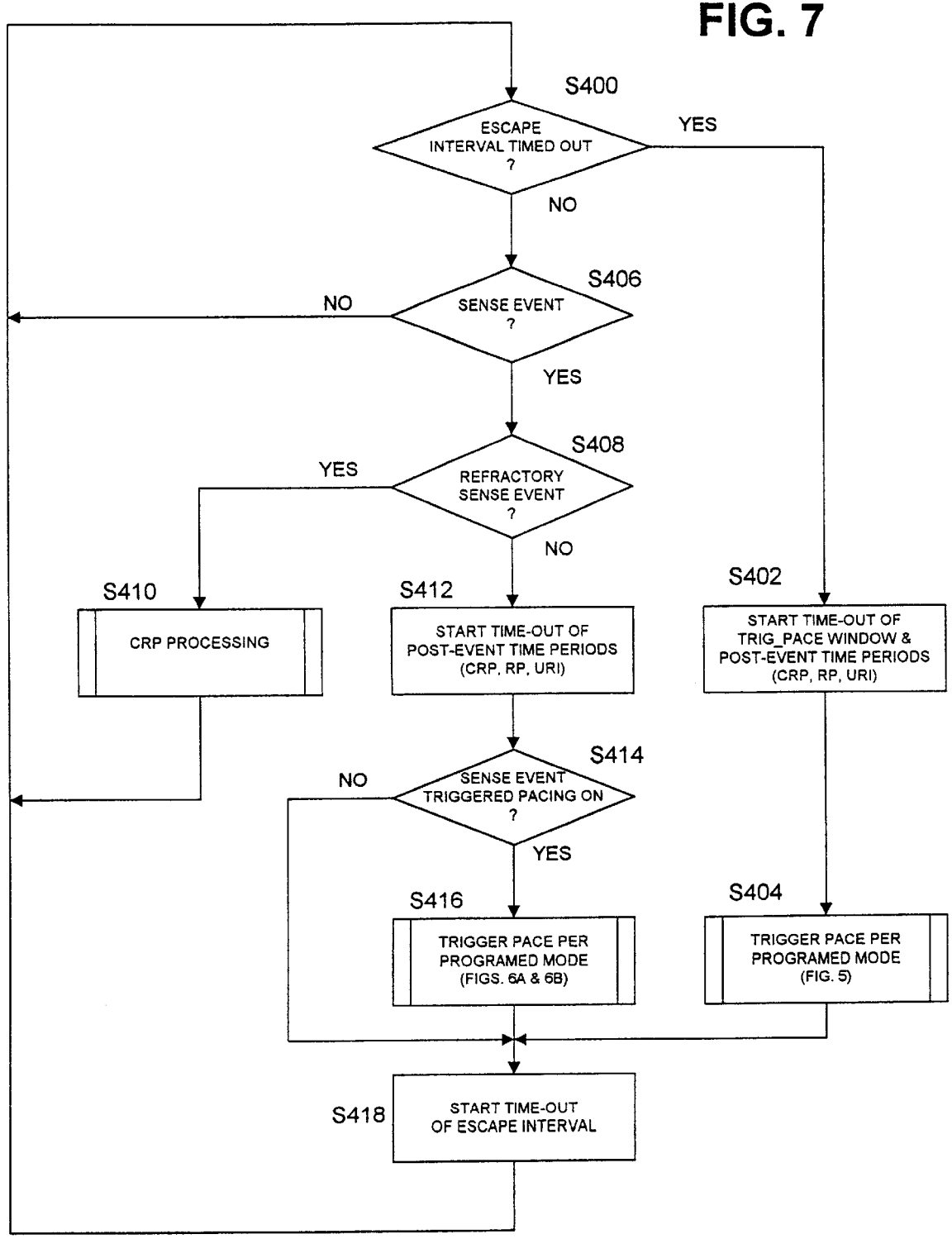

BI-CHAMBER CARDIAC PACING SYSTEM EMPLOYING UNIPOLAR LEFT HEART CHAMBER LEAD IN COMBINATION WITH BIPOLAR RIGHT CHAMBER LEAD

This patent application claims the benefit of U.S. Provisional Application No. 60/114090 filed Dec. 29, 1998 and No. 60/145860 filed Jul. 28, 1999.

CROSS-REFERENCE TO RELATED APPLICATIONS

Reference is hereby made to the following, commonly assigned, co-pending, U.S. Patent Applications which disclose common subject matter: Ser. No. 09/067,729 filed Apr. 28, 1998 for MULTIPLE CHANNEL, SEQUENTIAL, CARDIAC PACING SYSTEMS filed in the names of C. Struble et al.; Serial No. 09/439,244 filed on event date herewith for MULTI-SITE CARDIAC PACING SYSTEM HAVING CONDITIONAL REFRACTORY PERIOD filed in the names of K. Kleckner et al.; Serial No. 09/439,078 filed on even date herewith for MULTI-SITE CARDIAC PACING SYSTEM HAVING TRIGGER PACE WINDOW in the names of C. Juran et al.; Serial No. 09/439,569 filed on even date herewith for CARDIAC PACING SYSTEM DELIVERING MULTI-SITE PACING IN A PREDETERMINED SEQUENCE TRIGGERED BY A SENSE EVENT in the names of C. Yerich et al.; Serial No. 09/439,568 filed on even date herewith for RECHARGE CIRCUITRY FOR MULTI-SITE STIMULATION OF BODY TISSUE filed in the names of B. Blow et al.; and Serial No. 09/439,243 filed on even date herewith for AV SYNCHRONOUS CARDIAC PACING SYSTEM DELIVERING MULTI-SITE VENTRICULAR PACING TRIGGERED BY A VENTRICULAR SENSE EVENT DURING THE AV DELAY in the names of C. Yerich et al.

FIELD OF THE INVENTION

The present invention pertains to multi-site cardiac pacing systems for pacing right and left heart chambers in inhibited and triggered pacing modes employing combinations of right and left heart chamber pace/sense electrodes for providing left heart chamber pacing and sensing to facilitate placement of the left heart chamber pace/sense electrode at a left heart chamber pace/sense site that is difficult to access.

BACKGROUND OF THE INVENTION

In diseased hearts having conduction defects and in congestive heart failure (CHF), cardiac depolarizations that naturally occur in one upper or lower heart chamber are not conducted in a timely fashion either within the heart chamber or to the other upper or lower heart chamber. In patients suffering from CHF, the hearts may become dilated, and the conduction and depolarization sequences of the heart chambers may exhibit Intra-Atrial Conduction Defects (IACD), Left Bundle Branch Block (LBBB), Right Bundle Branch Block (RBBB), and Intra Ventricular Conduction Defects (IVCD). In such cases, the right and left heart chambers do not contract in optimum synchrony with each other, and cardiac output suffers due to the conduction defects. In addition, spontaneous depolarizations of the left atrium or left ventricle occur at ectopic foci in these left heart chambers, and the natural activation sequence is grossly disturbed. In such cases, cardiac output deteriorates because the contractions of the right and left heart chambers are not synchronized sufficiently to eject blood therefrom. Furthermore, significant conduction disturbances between the right and left atria can result in left atrial flutter or fibrillation.

It has been proposed that various conduction disturbances involving both bradycardia and tachycardia of a heart chamber could benefit from pacing pulses applied at multiple electrode sites positioned in or about a single heart chamber or in the right and left heart chambers in synchrony with a depolarization which has been sensed at a minimum of at least one of the electrode sites. It is believed that cardiac output can be significantly improved when left and right chamber synchrony is restored, particularly in patients suffering from dilated cardiomyopathy and CHF.

A number of proposals have been advanced for providing pacing therapies to alleviate these conditions and restore synchronous depolarization and contraction of a single heart chamber or right and left, upper and lower, heart chambers as described in detail in commonly assigned U.S. Pat. Nos. 5,403,356, 5,797,970 and 5,902,324 and in 5,720,768 and 5,792,203 all incorporated herein by reference. The proposals appearing in U.S. Pat. Nos. 3,937,226, 4,088,140, 4,548, 203, 4,458,677, 4,332,259 are summarized in U.S. Pat. Nos. 4,928,688 and 5,674,259, all incorporated herein by reference. The advantages of providing sensing at pace/sense electrodes located in both the right and left heart chambers is addressed in the '688 and '259 patents, as well as in U.S. Pat. Nos. 4,354,497, 5,174,289, 5,267,560, 5,514,161, and 5,584,867, also all incorporated herein by reference.

The medical literature also discloses a number of approaches of providing bi-atrial and/or bi-ventricular pacing as set forth in: Daubert et al., "Permanent Dual Atrium Pacing in Major Intra-atrial Conduction Blocks: A Four Years Experience", PACE (Vol.16, Part II, NASPE Abstract 141, p.885, April 1993); Daubert et al., "Permanent Left Ventricular Pacing With Transvenous Leads Inserted Into The Coronary Veins", PACE (Vol. 21, Part II, pp. 239–245, January 1998); Cazeau et al., "Four Chamber Pacing in Dilated Cardiomyopathy", PACE (Vol. 17, Part II, pp. 1974–1979, November 1994); and Daubert et al., "Renewal of Permanent Left Atrial Pacing via the Coronary Sinus", PACE (Vol. 15, Part II, NASPE Abstract 255, p. 572, April 1992), all incorporated herein by reference.

In the above-incorporated '768 patent, bipolar right heart chamber leads and unipolar left heart chamber leads are employed. Sensing of right heart depolarizations of the right heart chamber is effected between right heart chamber active tip and indifferent ring electrodes on the bipolar right heart lead. Sensing of the left heart chamber depolarizations is effected between a single left heart chamber active tip pace/sense electrode and the right heart chamber active tip pace/sense electrode. Then, sensing is switched to a unipolar mode to determine the true chamber of origin of the sensed left heart depolarization. Right and left heart chamber pacing to the other heart chamber is effected in a unipolar manner, employing the IPG housing or canister as an indifferent IPG "can" electrode.

In the above-incorporated '970 patent, bipolar left and right heart chamber pacing leads are employed that are coupled to a single sense amplifier and pacing output amplifier for sensing right and left heart depolarizations and providing right and left heart chamber pacing pulses. When sensing, the right and left heart chamber active tip pace/sense electrodes are coupled together to one input of the sense amplifier, and the right and left heart chamber indifferent ring pace/sense electrodes are coupled together to the other input of the sense amplifier. When pacing the right heart chamber, the right and left heart chamber indifferent ring pace/sense electrodes are coupled together, and a low energy pacing pulse is delivered through the right heart chamber active tip electrode. When pacing the left heart chamber, the right and left heart chamber indifferent ring pace/sense electrodes are coupled together, and a high energy pacing pulse is delivered through both the right and left heart chamber active tip electrodes. The pacing pulse energy is distributed along multiple pacing vectors, and in fact both the right and left heart chambers are simultaneously paced.

It is important that pacing energy be directed in a vector that maximizes efficiency of capturing the heart. In addition, the location of a left ventricular distal active pace/sense electrode deep in a cardiac vein within the narrow vessel lumen necessitates use of very small diameter unipolar lead bodies that do not allow inclusion of an indifferent ring electrode and associated lead conductor and insulation separating it from the lead conductor for the active pace/sense electrode. Since the active pace/sense electrode is separated from direct contact with the left ventricular myocardium, the left ventricular pacing threshold is likely to be higher than the right ventricular pacing threshold requiring a higher energy left ventricular pacing pulse than right ventricular pacing pulse. It is desirable to direct the left ventricle pacing pulse in a left ventricular pacing vector that traverses as great a bulk of the left ventricular myocardial mass as possible. It is undesirable to dissipate that pacing pulse energy in the right ventricle as is the case in approach disclosed in the '970 patent or to direct it through a vector traversing only a portion of the left ventricle to the remotely located indifferent IPG can electrode as is the case in the unipolar pacing modes disclosed in the above-incorporated '768 patent.

In the case of bi-atrial pacing systems, it is also desirable to direct the left atrial pacing pulse in an efficient left atrial pacing vector and to not dissipate pacing energy in body tissue or in the right atrium.

SUMMARY OF THE INVENTION

The present invention is therefore directed to providing right and left heart chamber pacing systems and methods of operation that provide efficient pacing of the left heart chamber without dissipating left heart chamber pacing energy.

In a bi-chamber pacing system, an IPG optionally having an indifferent IPG can electrode is coupled to a small diameter, unipolar, left heart chamber (LHC) endocardial lead and a bipolar right heart chamber (RHC) endocardial lead. The LHC lead is advanced through a venous pathway to locate the LHC active pace/sense electrode at a desired LHC pace/sense site. The RHC lead is advanced into the RHC chamber to locate RHC active and indifferent pace/sense electrodes therein. Sensing of RHC spontaneous cardiac depolarizations to provide a RHC sense event signal and delivery of RHC pacing pulses is conducted across the RHC active pace/sense electrode and one of the RHC or IPG indifferent pace/sense electrodes. Sensing of LHC spontaneous cardiac depolarizations to provide a LHC sense event signal is conducted across the LHC active pace/sense electrode and one of the RHC active or indifferent pace/sense electrodes or the IPG indifferent can electrode. Delivery of LHC pacing pulses is conducted across the LHC active pace/sense electrode and the RHC indifferent pace/sense electrode, whereby the LHC pacing vector traverses the mass of the LHC.

In a bi-ventricular pacing system, a small diameter, unipolar, left ventricular, coronary sinus (LV CS) endocardial lead and a bipolar right ventricular (RV) endocardial lead are preferably employed to provide the LHC and RHC pace/sense electrodes. The LV CS lead is advanced through the superior vena cava, the right atrium, the ostium of the coronary sinus (CS), the CS, and into a coronary vein descending from the CS to locate the LV active pace/sense electrode at a desired LV pace/sense site. The RV lead is advanced into the RV chamber to locate RV active and indifferent pace/sense electrodes therein. Sensing of RV spontaneous cardiac depolarizations to provide a RV sense event signal and delivery of RV pacing pulses is conducted across the RV active pace/sense electrode and one of the RV or IPG indifferent pace/sense electrodes. Sensing of LV spontaneous cardiac depolarizations to provide a LV sense event signal is conducted in a unipolar sensing vector across the LV active pace/sense electrode and the IPG indifferent pace/sense electrode or in a trans-ventricular sensing vector across the LV active pace/sense electrode and one of the RV active or indifferent pace/sense electrodes. Delivery of LV pacing pulses is conducted across the LV active pace/sense electrode and the RV indifferent pace/sense electrode and in a pacing vector that encompasses the bulk of the LV.

In a bi-atrial pacing system, a unipolar, left atrial, coronary sinus (LA CS) lead and a bipolar right atrial (RA) endocardial lead are preferably employed to provide the LHC and RHC pace/sense electrodes. Use of epicardial leads is of course an option. The unipolar LA CS (or epicardial) lead locates an active LA pace/sense electrode in relation to the LA, and the bipolar RA lead locates an active RA pace/sense electrode and indifferent RA pace/sense electrode in relation to the RA. Sensing of LA spontaneous cardiac depolarizations to provide a LA sense event signal is conducted across the LA active pace/sense electrode and one of the RA active or indifferent pace/sense electrodes or the IPG indifferent pace/sense electrodes. Delivery of LA pacing pulses is conducted across the LA active pace/sense electrode and the RA indifferent pace/sense electrode and in a pacing vector that encompasses the bulk of the LA.

In the context of bi-atrial or bi-ventricular pacing systems and methods, a number of triggered pacing modes are possible. In one triggered pacing mode, a first pacing pulse can be delivered to the RHC or LHC and a second pacing pulse delivered to the LHC or RHC, respectively, after a triggered pacing delay. The two pacing pulses can be delivered either upon a non-refractory sense event detected in one of the heart chambers or upon timeout of a pacing escape interval. Alternatively, following a non-refractory sense event in the RHC or LHC, a single pacing pulse can be delivered to the LHC or RHC, respectively after time-out of the triggered pacing delay timed from the sense event. In still another triggered pacing mode, a single pacing pulse can be delivered to the RHC or LHC where the non-refractory sense event is detected.

The present invention is preferably implemented in systems for providing atrial or ventricular bi-chamber pacing or AV synchronous pacing systems for providing three or four chamber pacing.

The present invention is also preferably implemented into an external or implantable pulse generator and lead system selectively employing right and left heart, atrial and/or ventricular leads. The preferred embodiment is implemented in an architecture that allows wide programming flexibility for operating in AV synchronous modes with right and left ventricular pacing or in atrial or ventricular only modes for providing only right and left atrial or ventricular pacing. The AV synchronous embodiments may be implemented into an IPG or external pulse generator and lead system providing right and left ventricular pacing and sensing and either both right and left atrial pacing or just right or left atrial pacing and sensing. Alternatively, the invention can be implemented in IPGs or external pulse generators and lead systems having hard wired connections and operating modes that are not as programmable.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIGS. 6A–6B is a flow chart illustrating the steps of delivering ventricular pacing pulses following a ventricular sense event during the time-out of an AV delay or the V-A escape interval in FIG. 4; and FIG. 7 is a comprehensive flow-chart illustrating the operating modes of the IPG circuitry of FIG. 3 in a variety of bi-atrial or bi-ventricular pacing modes in accordance with a further embodiment of the invention selectively employing steps of FIGS. 5 and 6 therein.

DETAILED DESCRIPTION OF THE PREFERRED EMBODIMENTS

In the following detailed description, references are made to illustrative embodiments for carrying out the invention. It is understood that other embodiments may be utilized without departing from the scope of the invention. For example, the invention is disclosed in detail in FIGS. 2 and 3 in the context of an AV sequential, bi-ventricular, pacing system operating in demand, atrial tracking, and triggered pacing modes in accordance with FIGS. 4 through 6A–6B for restoring synchrony in depolarizations and contraction of left and right ventricles in synchronization with atrial sensed and paced events for treating bradycardia in those chambers. This embodiment of the invention is programmable to operate as a three or four channel pacing system having an AV synchronous operating mode for restoring upper and lower heart chamber synchronization and right and left atrial and/or ventricular chamber depolarization synchrony. But, it will be realized that the invention can also be practiced in a bi-ventricular or bi-atrial pacing system that can be dedicated to such use or can be a programmable mode of the system of FIGS. 2 and 3 following the flow chart of FIG. 7. The invention can be practiced in a two channel or four channel pacing system of the type disclosed in the above-incorporated '324 patent as well.

It should be appreciated that the present invention may be utilized particularly to treat patients suffering CHF and bradycardia. The pacing system of the present invention may also may be incorporated into an anti-tachyarrhythmia system including specific high rate pacing and cardioversion shock therapies for providing staged therapies to treat a diagnosed arrhythmia.

Figure 1:
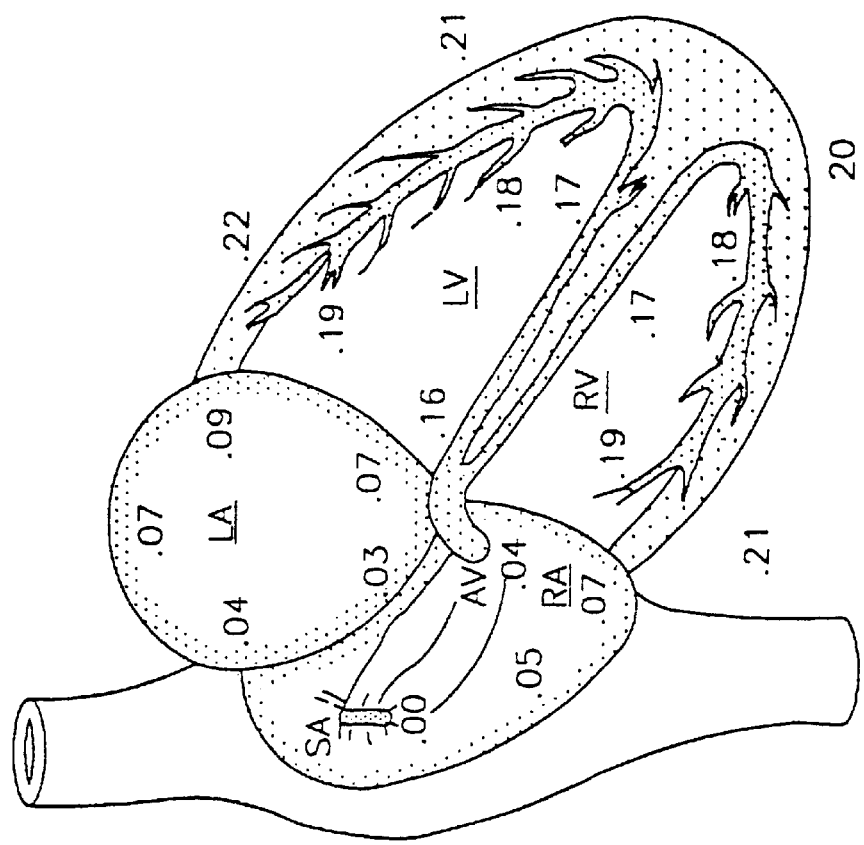
FIG. 1 is an illustration of transmission of the cardiac depolarization waves through the heart in a normal electrical activation sequence.

In FIG. 1, heart 10 includes the upper heart chambers, the right atrium (RA) and left atrium (LA), and the lower heart chambers, the right ventricle (RV) and left ventricle (LV) and the coronary sinus (CS) extending from the opening in the right atrium laterally around the atria to form the cardiac veins. FIG. 1 is an illustration of transmission of the cardiac depolarization waves through the RA, LA, RV and LV in a normal electrical activation sequence at a normal heart rate with the conduction times exhibited thereon in seconds. The cardiac cycle commences normally with the generation of the depolarization impulse at the SA Node in the right atrial wall and its transmission through the atrial conduction pathways of Bachmann's Bundle and the Internodal Tracts at the atrial level into the left atrial septum. The RA depolarization wave reaches the Atrio-ventricular (AV) node and the atrial septum within about 40 msec and reaches the furthest walls of the RA and LA within about 70 msec, and the atria complete their contraction as a result. The aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent the RA or LA is also referred to as a sensed P-wave. Although the location and spacing of the external ECG electrodes or implanted unipolar atrial pace/sense electrodes has some influence, the normal P-wave width does not exceed 80 msec in width as measured by a high impedance sense amplifier coupled with such electrodes. A normal near field P-wave sensed between closely spaced bipolar pace/sense electrodes and located in or adjacent the RA or the LA has a width of no more than 60 msec as measured by a high impedance sense amplifier.

The depolarization impulse that reaches the AV Node is distributed inferiorly down the bundle of His in the intraventricular septum after a delay of about 120 msec. The depolarization wave reaches the apical region of the heart about 20 msec later and then travels superiorly though the Purkinje Fiber network over the remaining 40 msec. The aggregate RV and LV depolarization wave and the subsequent T-wave accompanying repolarization of the depolarized myocardium are referred to as the QRST portion of the PQRST cardiac cycle complex when sensed across external ECG electrodes and displayed. When the amplitude of the QRS ventricular depolarization wave passing between a bipolar or unipolar pace/sense electrode pair located on or adjacent the RV or LV exceeds a threshold amplitude, it is detected as a sensed R-wave. Although the location and spacing of the external ECG electrodes or implanted unipolar ventricular pace/sense electrodes has some influence, the normal R-wave width does not exceed 80 msec in width as measured by a high impedance sense amplifier. A normal near field R-wave sensed between closely spaced bipolar pace/sense electrodes and located in or adjacent the RV or the LV has a width of no more than 60 msec as measured by a high impedance sense amplifier.

The typical normal conduction ranges of sequential activation are also described in the article by Durrer et al., entitled "Total Excitation of the Isolated Human Heart", in CIRCULATION (Vol. XLI, pp. 899–912, June 1970). This normal electrical activation sequence becomes highly disrupted in patients suffering from advanced CHF and exhibiting IACD, LBBB, RBBB, and/or IVCD. These conduction defects exhibit great asynchrony between the RV and the LV due to conduction disorders along the Bundle of His, the Right and Left Bundle Branches or at the more distal Purkinje Terminals. Typical intra-ventricular peak—peak asynchrony can range from 80 to 200 msec or longer. In RBBB and LBBB patients, the QRS complex is widened far beyond the normal range to from >120 msec to 250 msec as measured on surface ECG. This increased width demonstrates the lack of synchrony of the right and left ventricular depolarizations and contractions.

In accordance with a first embodiment of the present invention, a method and apparatus is provided to restore the depolarization sequence of FIG. 1 and the synchrony between the right and left ventricular heart chambers that contributes to adequate cardiac output. This restoration is effected through providing optimally timed cardiac pacing pulses to the right and left ventricles as necessary and to account for the particular implantation sites of the pace/sense electrodes in relation to each heart chamber while maintaining AV synchrony. The present invention efficiently directs the left heart chamber pacing pulses in a desirable pacing vector that encompasses the bulk of the left heart chamber and facilitates placement of the left heart chamber pace/sense electrodes at desired pace/sense sites of the left heart chamber.

Figure 2:
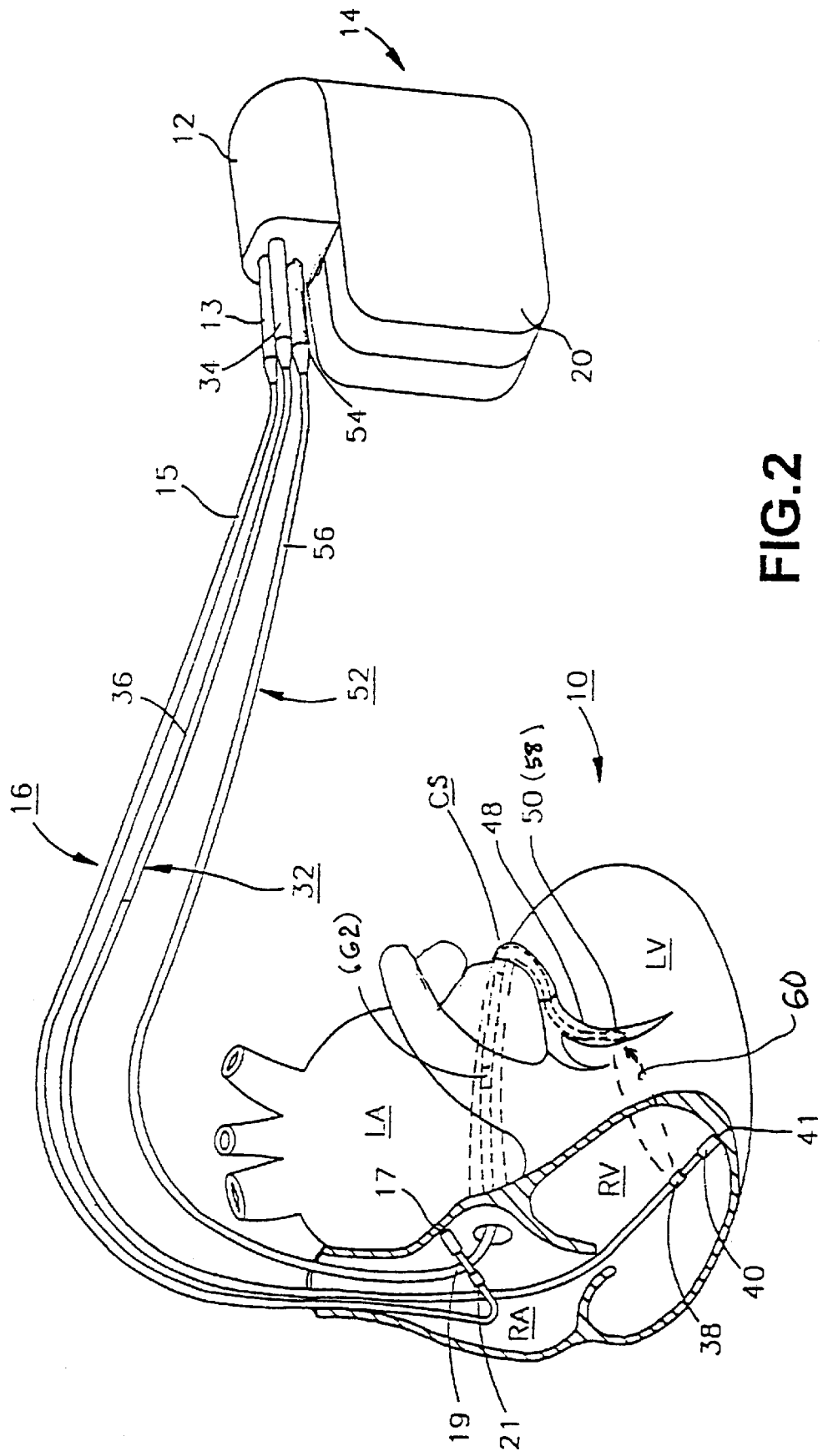
FIG. 2 is a schematic diagram depicting a three channel, atrial and bi-ventricular, pacing system in which the present invention is preferably implemented.

FIG. 2 is a schematic representation of an implanted, three channel cardiac pacemaker of the above noted types for restoring AV synchronous contractions of the atrial and ventricular chambers and simultaneous or sequential pacing of the right and left ventricles. The Implantable Pulse Generator IPG 14 is implanted subcutaneously in a patient's body between the skin and the ribs. Three endocardial leads 16, 32 and 52 connect the IPG 14 with the RA, the RV and the LV, respectively. Each lead has at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions. The depicted positions in or about the right and left heart chambers are also merely exemplary. For instance, any of the leads may be placed epicardially if desired, or there may be other arrangements made. Moreover other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a unipolar, endocardial LV CS lead 52 is passed through a vein and the RA chamber of the heart 10, into the CS and then inferiorly in a branching vessel of the cardiac vein 48 to extend the distal LV CS pace/sense electrode 50 alongside the LV chamber. The distal end of such LV CS leads is advanced through the superior vena cava, the right atrium, the ostium of the coronary sinus, the coronary sinus, and into a coronary vein descending from the coronary sinus, such as the cardiac vein. Typically, LV CS leads and LA CS leads do not employ any fixation mechanism and instead rely on the close confinement within these vessels to maintain the pace/sense electrode or electrodes at a desired site. The LV CS lead 52 is formed with a small diameter single conductor lead body 56 coupled at the proximal end connector 54 fitting into a bore of IPG connector block 12. A small diameter unipolar lead body 56 is selected in order to lodge the distal LV CS pace/sense electrode 50 deeply in a vein branching inferiorly from the great vein 48.

In accordance with the present invention, the distal, LV CS active pace/sense electrode 50 is paired with the proximal ring RV indifferent pace/sense electrode 38 for delivering LV pace pulses across the bulk of the left ventricle and the intraventricular septum. The distal LV CS active pace/sense electrode 50 is also preferably paired with the distal tip RV active pace/sense electrode 40 for sensing across the RV and LV as described further below.

Moreover, in a four chamber embodiment, LV CS lead 52 could bear a proximal LA CS pace/sense electrode positioned along the lead body to lie in the larger diameter coronary sinus CS adjacent the LA. In that case, the lead body 56 would encase two electrically insulated lead conductors extending proximally from the more proximal LA CS pace/sense electrode(s) and terminating in a bipolar connector 54. The LV CS lead body would be smaller between the proximal LA CS electrode and the distal LV CS active pace/sense electrode 50. In that case, pacing of the RA would be accomplished along the pacing vector between the active proximal LA CS active electrode and the proximal ring RA indifferent pace/sense electrode 21.

Figure 3:
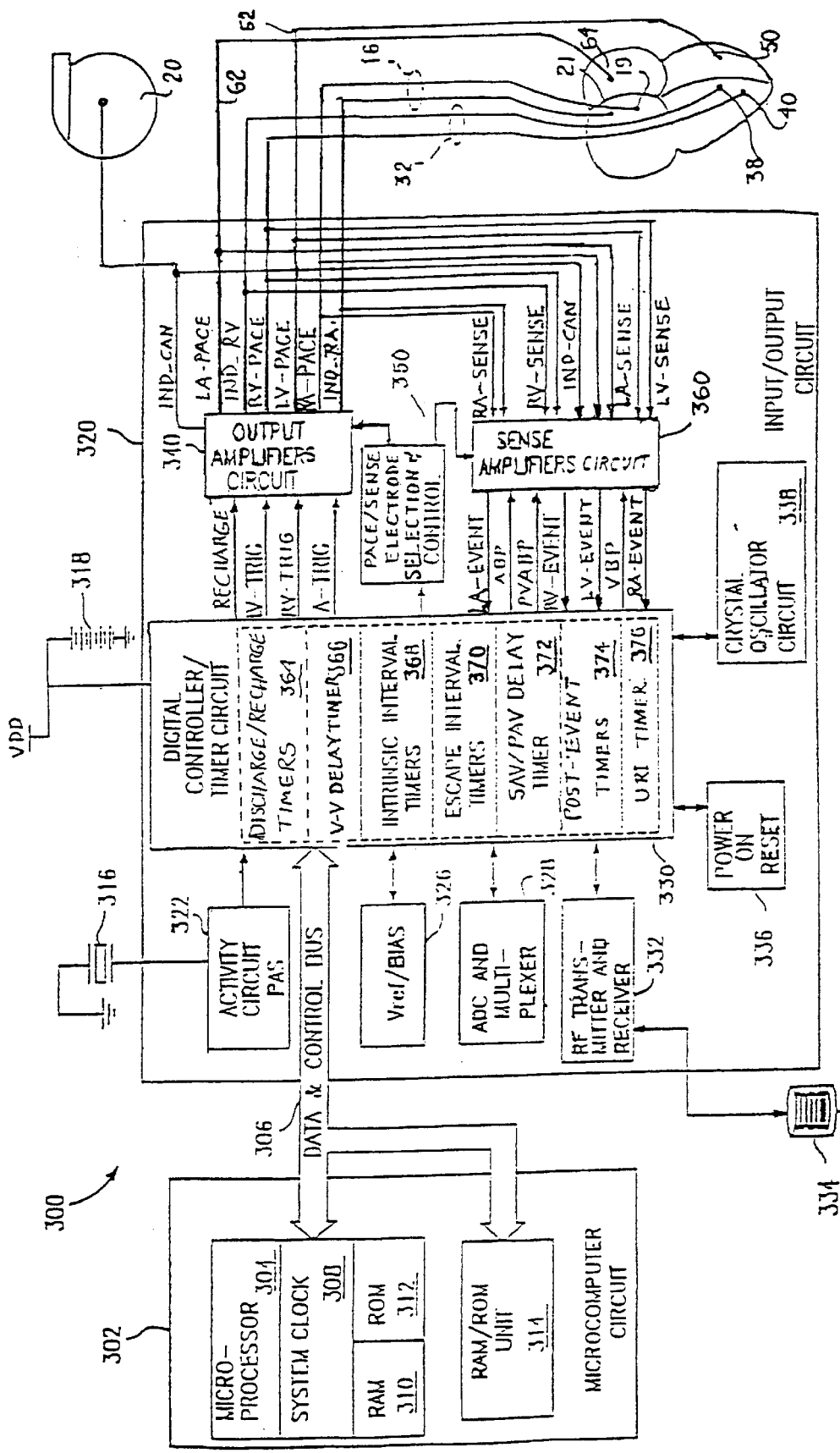
FIG. 3 is a simplified block diagrams of one embodiment of IPG circuitry and associated leads employed in the system of FIG. 2 for providing four pacing channels that are selectively programmed in bi-atrial and/or bi-ventricular pacing modes.

FIG. 3 depicts bipolar RA lead 16, optional unipolar LA lead 62, bipolar RV lead 32, and unipolar LV CS lead 52 coupled with an IPG circuit 300 having programmable modes and parameters and a telemetry transceiver of a DDDR type known in the pacing art. A unipolar LA pace/sense electrode 64 is provided at the distal end of the LA CS lead 62. The unipolar LA lead 62 may also be a CS lead and may be formed as part of the LV CS lead 52 as described above. The IPG circuit 300 is illustrated in a functional block diagram divided generally into a microcomputer circuit 302 and a pacing circuit 320. The pacing circuit 320 includes the digital controller/timer circuit 330, the output amplifiers circuit 340, and the sense amplifiers circuit 360, as well as a number of other circuits and components described below.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexer circuit 328 digitizes analog signals and voltage to provide real time telemetry if a cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 322 in the depicted, exemplary IPG circuit 300. The patient activity sensor 316 is coupled to the implantable pulse generator housing 118 and may take the form of a piezoelectric crystal transducer as is well known in the art and its output signal is processed and used as the RCP. A timed interrupt, e.g., every two seconds, may be provided in order to allow the microprocessor 304 to analyze the output of the activity circuit PAS 322 and update the basic V-A (or A-A or V-V) escape interval employed in the pacing cycle.

Data transmission to and from the external programmer is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 normally operates in a reduced power consumption mode and is interrupt driven. Microprocessor 304 is awakened in response to defined interrupt events, which may include A-PACE, RV-PACE, LV-PACE signals generated by timers in digital timer/controller circuit 330 and A-EVENT, RV-EVENT, and LV-EVENT signals generated by sense amplifiers circuit 360, among others. The specific values of the intervals and delays timed out by digital controller/timer circuit 330 are controlled by the microcomputer circuit 302 by means of data and control bus 306 from programmed-in parameter values and operating modes.

In one embodiment of the invention, microprocessor 304 is a custom microprocessor adapted to fetch and execute instructions stored in RAM/ROM unit 314 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 304.

Digital controller/timer circuit 330 operates under the general control of the microcomputer 302 to control timing and other functions within the pacing circuit 320 and includes a set of timing and associated logic circuits of which certain ones pertinent to the present invention are depicted. The depicted timing circuits include discharge/recharge timers 364, V-V delay timer 366, an intrinsic interval timer 368 for timing elapsed V-EVENT to V-EVENT intervals or V-EVENT to A-EVENT intervals, escape interval timers 370 for timing A-A, V-A, and/or V-V pacing escape intervals, an AV delay interval timer 372 for timing an AV delays from a preceding A-EVENT (SAV) or A-PACE (PAV), a post-ventricular timer 374 for timing post-ventricular time periods, and an upper rate interval (URI) timer 376. RHC pace trigger and sense events are typically used for starting and resetting these intervals and periods. However, it would be possible to allow the physician to select and program LHC pace trigger and sense events for these timing purposes.

Microcomputer 302 controls the operational functions of digital controller/timer circuit 330, specifying which timing intervals are employed, and setting at least the programmed-in base timing intervals, via data and control bus 306. Digital controller/timer circuit 330 starts and times out these intervals and delays for controlling operation of the atrial and ventricular sense amplifiers in sense amplifiers circuit 360 and the atrial and ventricular pace pulse generators in output amplifiers circuit 340.

The post-event timers 374 time out the post-ventricular time periods following an RV-EVENT or LV-EVENT or a RV-PACE or LV-PACE and post-atrial time periods following an A-EVENT or A-PACE. The durations of the post-event time periods may also be selected as programmable parameters stored in the microcomputer 302. The post-ventricular time periods include the PVARP, a post-atrial ventricular blanking period (PAVBP), a ventricular blanking period (VBP), a ventricular refractory period (VRP), and a conditional ventricular refractory period (CVRP). The post-atrial time periods include an atrial refractory period (ARP) during which an A-EVENT is ignored for the purpose of resetting the AV delay, and an atrial blanking period (ABP) during which atrial sensing is disabled. These post-atrial time periods time out concurrently with the time-out of the SAV or PAV delay started by an A-EVENT or an A-PACE.

It should be noted that the starting of the post-atrial time periods and the AV delays can be commenced substantially simultaneously with the start or end of the A-EVENT or A-PACE. Similarly, the starting of the post-ventricular time periods and the V-A escape interval can be commenced substantially simultaneously with the start or end of the V-EVENT or V-PACE.

The microprocessor 304 also optionally calculates AV delays, post-ventricular time periods, and post-atrial time periods which vary with the sensor based escape interval established in response to the RCP(s) and/or with the intrinsic atrial rate. The variable AV delays are usually derived as an offset of a maximum AV delay set for the pacing lower rate (i.e., the longest escape interval).

The output amplifiers circuit 340 contains a RA pace pulse generator, a LA pace pulse generator, a RV pace pulse generator and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 330 generates a RV-TRIG or LV-TRIG signal at the end of an AV delay provided by AV delay interval timer 372. Similarly, in order to trigger a right or left atrial pacing or RA-PACE pulse or LA-PACE pulse, digital controller/timer circuit 330 generates an RA-TRIG or LA-TRIG signal at the end of the V-A escape interval timed by escape interval timers 370.

Typically, in pacing systems of the type illustrated in FIGS. 2 and 3, the electrodes designated above as "pace/sense" electrodes are used for both pacing and sensing functions. In accordance with one aspect of the present invention, these "pace/sense" electrodes can be selected to be used exclusively as pace or sense electrodes or to be used in common as pace/sense electrodes in programmed combinations for sensing cardiac signals and delivering pacing pulses along pacing and sensing vectors. Separate or shared indifferent pace and sense electrodes can also be designated in pacing and sensing functions. For convenience, the following description separately designates pace and sense electrode pairs where a distinction is appropriate.

The output amplifiers circuit 340 includes switching circuits for coupling selected pace electrode pairs from among the lead conductors and the IND_CAN electrode 20 to the RA pace pulse generator, LA pace pulse generator, RV pace pulse generator and LV pace pulse generator. Pace/sense electrode pair selection and control circuit 350 selects lead conductors and associated pace electrode pairs to be coupled with the atrial and ventricular output amplifiers within output amplifiers circuit 340 for accomplishing RA, LA, RV and LV pacing as described below.

The sense amplifiers circuit 360 contains sense amplifiers corresponding to any of those presently employed in commercially marketed cardiac pacemakers for atrial and ventricular pacing and sensing. As noted in the above-referenced, commonly assigned, '324 patent, it has been common in the prior art to use very high impedance P-wave and R-wave sense amplifiers to amplify the voltage difference signal which is generated across the sense electrode pairs by the passage of a cardiac depolarization. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 330 controls sensitivity settings of the atrial and ventricular sense amplifiers 360.

The sense amplifiers are uncoupled from the sense electrodes during the blanking periods before, during, and after delivery of a pacing pulse to any of the pace electrodes of the pacing system to avoid saturation of the sense amplifiers. The sense amplifiers circuit 360 includes blanking circuits for uncoupling the selected pairs of the lead conductors and the IND_CAN electrode 20 from the inputs of the RA sense amplifier, LA sense amplifier, RV sense amplifier and LV sense amplifier during the ABP, PVABP and VBP. The sense amplifiers circuit 360 also includes switching circuits for coupling selected sense electrode lead conductors and the IND_CAN electrode 20 to the RA sense amplifier, LA sense amplifier, RV sense amplifier and LV sense amplifier. Again, sense electrode selection and control circuit 350 selects conductors and associated sense electrode pairs to be coupled with the atrial and ventricular sense amplifiers within the output amplifiers circuit 340 and sense amplifiers circuit 360 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 330. Similarly, left atrial depolarizations or P-waves in the LA-SENSE signal that are sensed by the LA sense amplifier result in a LA-EVENT signal that is communicated to the digital controller/timer circuit 330. Ventricular depolarizations or R-waves in the RV-SENSE signal are sensed by a ventricular sense amplifier result in an RV-EVENT signal that is communicated to the digital controller/timer circuit 330. Similarly, ventricular depolarizations or R-waves in the LV-SENSE signal are sensed by a ventricular sense amplifier result in an LV-EVENT signal that is communicated to the digital controller/timer circuit 330. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

In accordance with the present invention, sensing of RHC (RA and/or RV) spontaneous cardiac depolarizations to provide a RHC sense event signal(RA-SENSE and/or RV-SENSE) and delivery of RHC pacing pulses (RA-PACE and/or RV-PACE) is conducted across the RHC active pace/sense electrode (9 and/or 40) and one of the RHC indifferent ring, pace/sense electrodes (21 and/or 38) or IPG indifferent pace/sense electrodes (IND_CAN 20). Sensing of LHC spontaneous cardiac depolarizations (LA-SENSE and/or LV-SENSE) to provide a LHC sense event signal (LA-EVENT and/or LV-EVENT) is conducted in a trans-ventricular sensing vector across the LHC active pace/sense electrode and one of the RHC active or indifferent pace/sense electrodes or the IPG indifferent can electrode. Delivery of LHC pacing pulses (LA-PACE and/or LV-PACE) is conducted across the LHC active pace/sense electrode (64 and/or 50) and the RHC indifferent ring pace/sense electrode (21 and/or 38), whereby the LHC pacing vector traverses the mass of the LHC.

Advantageously, the pacemaker of FIG. 3 could be simplified by providing only a single atrial sense amplifier coupled to a trans-atrial sense electrode pair comprising the active CS LA and the active RA pace/sense electrodes 64 and 19. Then, only a single A-EVENT would be provided and employed, and it may reflect either a RA-SENSE or a LA-SENSE. Similarly, the pacemaker could be simplified by providing only a single ventricular sense amplifier coupled to the active CS LV and the active distal tip RV pace/sense electrodes 50 and 40 to provide a single trans-ventricular sensing vector. Then, only a single V-EVENT would be provided and employed.

To simplify the description of FIGS. 4 through 6A–6B, it will be assumed that the following references to an "A-EVENT" and "A-PACE" will be the RA-EVENT and RA-PACE, respectively, if there is no LA pacing or sensing provided or programmed on, or will be a programmed one of the RA-EVENT or LA-EVENT and RA-PACE or LA-PACE, respectively. The A-EVENT could also be the output sense event signal of the single atrial sense amplifier coupled to active pace/sense electrodes 19 and 64.

Figure 4:
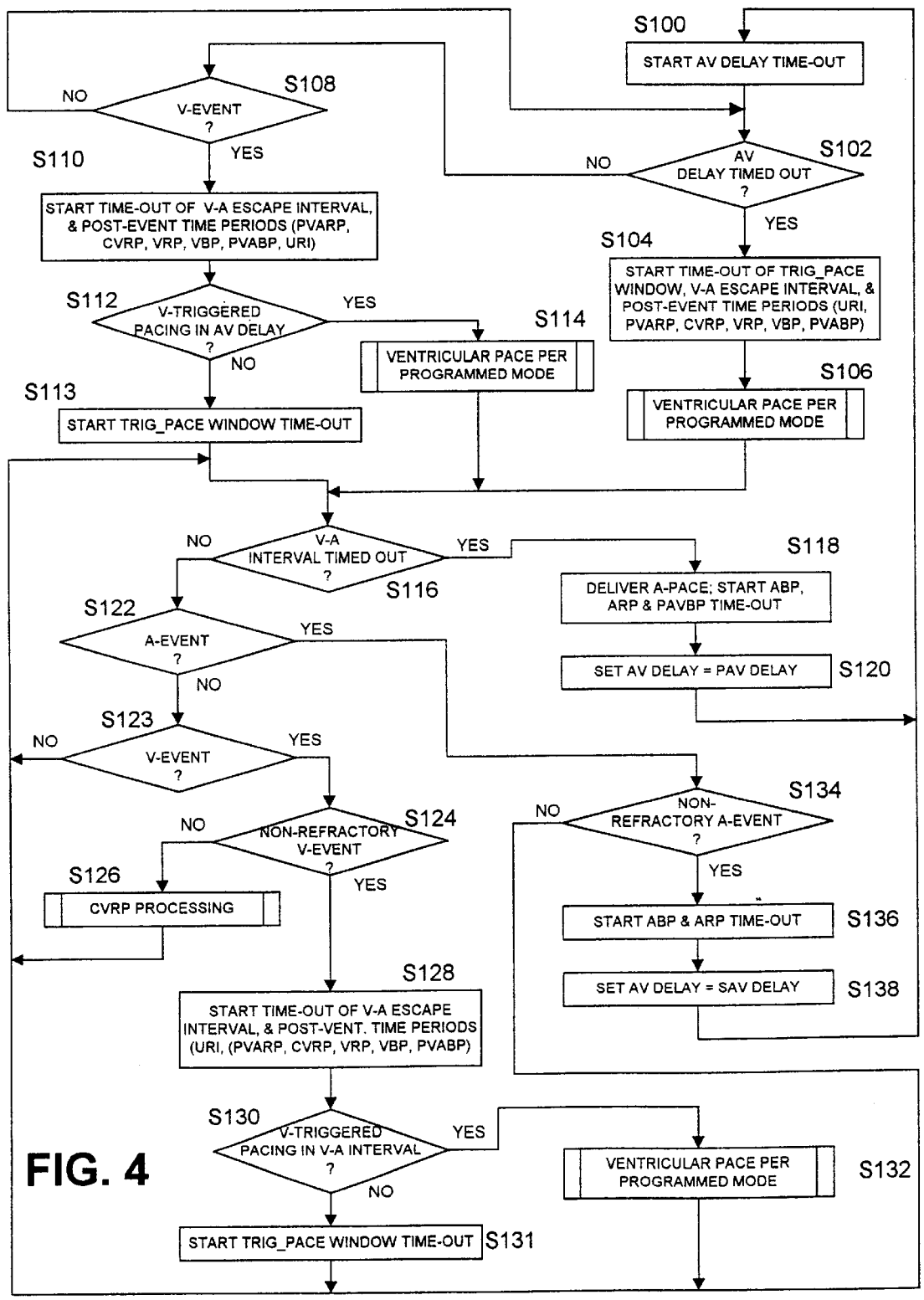
FIG. 4 is a comprehensive flow-chart illustrating the operating modes of the IPG circuitry of FIG. 3 in a variety of AV synchronous, bi-ventricular pacing modes in accordance with one embodiment of the invention.

The general operation of IPG circuit 300 is depicted in the flow chart of FIG. 4. The AV delay is started in step S100 when a P-wave outside of refractory is sensed across the selected atrial sense electrode pair during the V-A escape interval (an A-EVENT) as determined in step S134 or an A-PACE pulse is delivered to the selected atrial pace electrode pair in step S118. The AV delay can be a PAV or SAV delay, depending upon whether it is started on an A-PACE or an A-EVENT, respectively, and is timed out by the SAV/PAV delay timer 372. The SAV or PAV delay is terminated upon a non-refractory RV-EVENT or LV-EVENT output by a ventricular sense amplifier prior to its time-out.

The post-event timers 374 are started to time out the post-ventricular time periods and the TRIG_PACE window, and the V-A escape interval timer 370 is started to time out the V-A escape interval in step S104 if the SAV or PAV delay times out in step S102 without the detection of a non-refractory RV-EVENT or LV-EVENT. The TRIG_PACE window inhibits triggered pacing modes in response to a sense event occurring too early in the escape interval and is described in greater detail in the above-referenced application Ser. No. 09/439,078.

Figure 5:
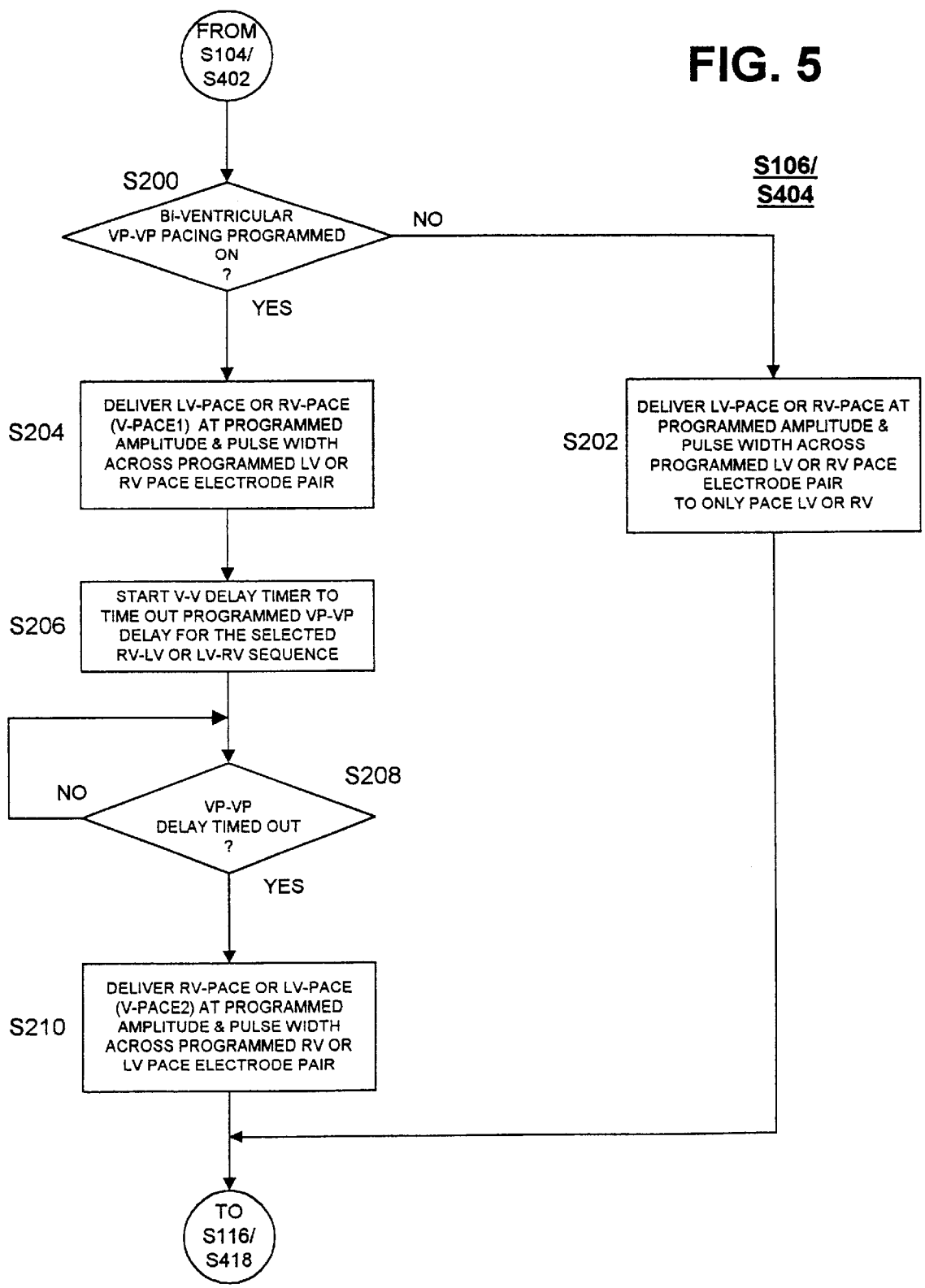
FIG. 5 is a flow chart illustrating the steps of delivering ventricular pacing pulses following time-out of an AV delay in FIG. 4.

Either a programmed one or both of the RV-PACE and LV-PACE pulses are delivered in step S106 (as shown in FIG. 5) to selected RV and LV pace electrode pairs, and the V-A escape interval timer is timed out in step S116. When both of the RV-PACE and LV-PACE pulses are delivered, the first is referred to as V-PACE1, the second is referred to as V-PACE2, and they are separated by a VP-VP delay. As described in greater detail below in reference to FIGS. 6A–6B, if a bi-ventricular pacing mode is programmed in step S106, it can be selectively programmed in a left-to-right or right-to-left ventricle pacing sequence wherein the first and second delivered ventricular pacing pulses are separated by separately programmed VP-VP delays. The VP-VP delays are preferably programmable between nearly 0 msec (say for example 4 msecs) and about 80 msec.

Figure 6A:
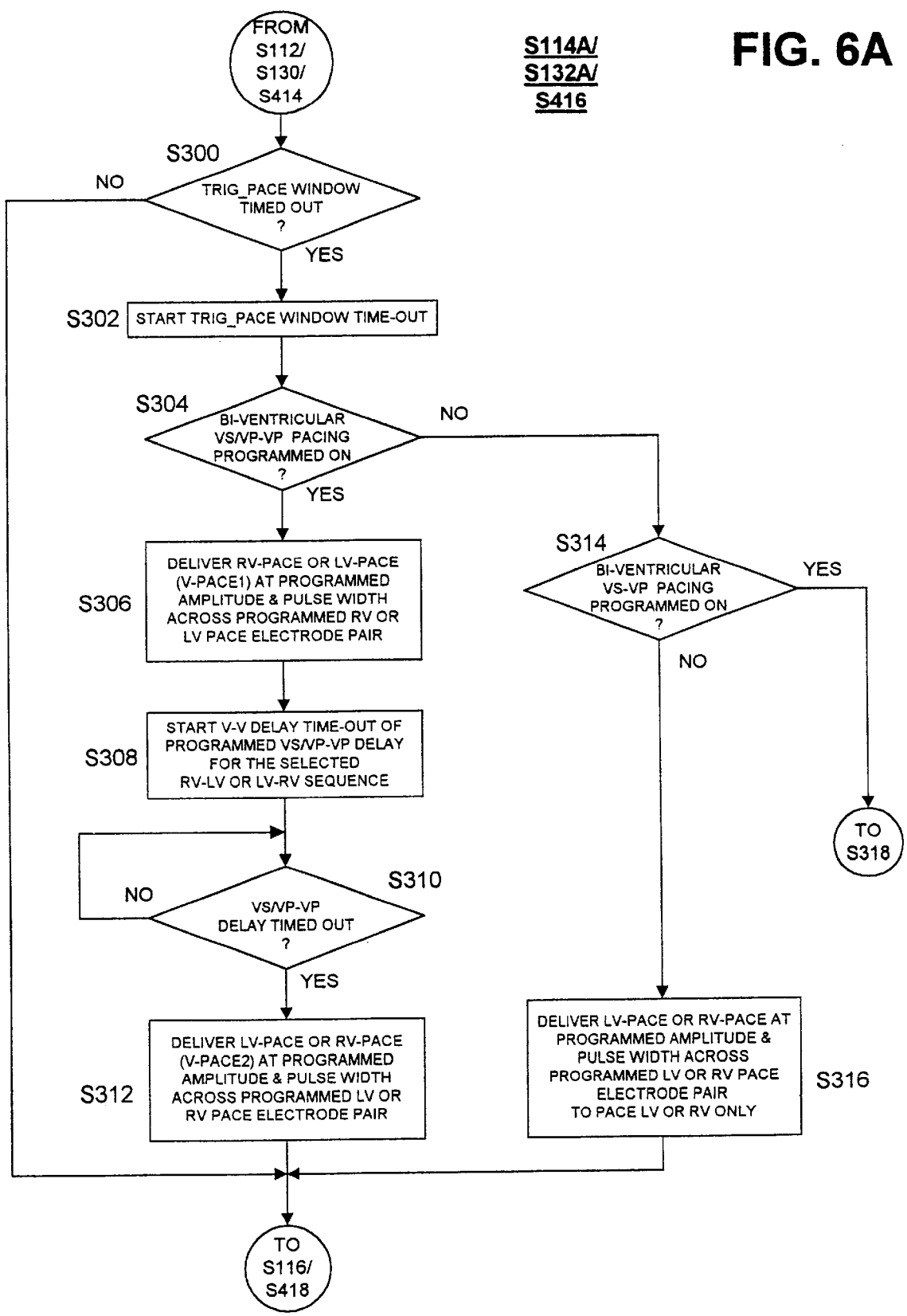

Returning to step S102, the AV delay is terminated if an RV-EVENT or LV-EVENT (collectively, a V-EVENT) is generated by the RV sense amplifier or the LV sense amplifier in step S108. The time-out of the V-A escape interval and the post-ventricular time periods are started in step S110 in response to the V-EVENT. In step S112, it is determined whether a ventricular triggered pacing mode is programmed to be operative during the AV delay. If one is programmed on, then it is undertaken and completed in step S114 (FIGS. 6A–6B). If a ventricular triggered pacing mode is not programmed on as determined in step S112, then no ventricular pacing is triggered by a sensed non-refractory V-EVENT terminating the AV delay. The time-out of the TRIG_PACE window is commenced in step S113 simultaneously with the time-out of the V-A escape interval and post-event time periods in step S110. The time-out of the TRIG_PACE window is commenced in step S113 simultaneously with the time-out of the V-A escape interval and post-event time periods in step S110.

If the V-A atrial escape interval is timed out by timer 370 in step S116 without a non-refractory A-EVENT being sensed across the selected pair of atrial sense electrodes, then the A-PACE pulse is delivered across the selected RA pace electrode pair in step S118, the AV delay is set to PAV in step S120, and the AV delay is commenced by AV delay timer 372.

If a non-refractory A-EVENT is generated as determined in steps S122 and S134, then the V-A escape interval is terminated. The ABP and ARP are commenced by post-event timers 374 in step S134, the AV delay is set to the SAV in step S138, and the SAV delay is started in step S100 and timed out by SAV/PAV delay timer 372.

Assuming that the normal activation sequence is sought to be restored, a programmed SAV and PAV delay corresponding to a normal AV conduction time from the AV node to the bundle of His are used or a calculated SAV and PAV delay is calculated in relation to the prevailing sensor rate or sensed intrinsic heart rate and are used by SAV/PAV delay timer 372.

If an RV-EVENT or LV-EVENT or a collective V-EVENT sensed across the RV tip sense electrode and the LV sense electrode (for simplicity, all referred to as a V-EVENT) is detected in step S123 during the time-out of the V-A escape interval, then, it is determined if it is a non-refractory V-EVENT or a refractory V-EVENT in step S124. If an RV-EVENT or LV-EVENT (collectively a V-EVENT) is sensed during the time-out of the V-A escape interval in step S123, then, it is determined if it is a non-refractory V-EVENT or a refractory V-EVENT in step S124. If the V-EVENT is determined to be a refractory V-EVENT in step S124, then it is employed in the CVRP processing step S126 which is described in detail in the above-referenced application Ser. No. 09/439,244. If the V-EVENT is determined to be a non-refractory V-EVENT in step S124, then the V-A escape interval is restarted, and the post-ventricular time periods are restarted in step S128.

In step S130, it is determined whether a triggered pacing mode is programmed to be operative during the V-A escape interval. If one is programmed on, then it is undertaken and completed in step S132 (FIGS. 6A–6B). If triggered pacing is not programmed on as determined in step S130, then no ventricular pacing is triggered by the sensed non-refractory V-EVENT during the V-A escape interval. The time-out of the TRIG_PACE window is commenced in step S131 simultaneously with the time-out of the V-A escape interval and post-event time periods in step S128.

FIG. 5 depicts the step S106 in greater detail, and FIGS. 6A–6B depict the steps S114 and S132 in greater detail. As described in greater detail below, if a VP-VP pacing mode is programmed on in step S106, it can be selectively programmed in a left-to-right or right-to-left ventricle sequence, wherein the first and second delivered ventricular pacing pulses (V-PACE1 and V-PACE2) are separated by separately programmed VP-VP delays. If a bi-ventricular triggered pacing mode is programmed on in either or both of steps S114 and S132, it can be selectively programmed to immediately pace the ventricle from which the V-EVENT is sensed or a fixed or programmed ventricle regardless of where the V-EVENT is sensed with a V-PACE1. Then, the V-PACE2 is generated to synchronously pace the other ventricle after a programmed VS/VP-VP delay. Or, the triggered pacing mode can be selectively programmed in either or both of steps S114 and 132 to only synchronously pace the other ventricle than the ventricle from which the V-EVENT is sensed with V-PACE2 after separately programmable VS-VP delays, depending on the right-to-left or left-to-right sequence. All of these VP-VP, VS/VP-VP, and VS-VP delays are preferably programmable between nearly 0 msec and about 80 msec. As a practical matter, the minimum VS/VP-VP, and VP-VP delays may be set to one half the system clock cycle in order to avoid simultaneous delivery of RV-PACE and LV-PACE pulses. The pacing pulse width is typically programmable between about 0.5 msec and 2.0 msec, and the pacing pulse amplitude is typically programmable between 0.5 and 7.5 volts. The system clock provides a full clock cycle of about 8.0 msec. Therefore, the minimum VP-VP delay is set at a half clock cycle or about 4.0 msec.

It is desired to be able to deliver RV-PACE and LV-PACE pulses that differ from one another in pulse width and amplitude in order to make certain that the delivered energy is sufficient to capture the heart chamber without being unduly wasteful of energy. But, if differing amplitude and pulse width RV-PACE and LV-PACE pulses are simultaneously delivered to the right and left ventricles, then DC current pathways can develop between the active electrodes that can cause aberrant conduction pathways in the heart and can lead to oxidation or other deterioration of the pace/sense electrodes.

In addition, when a pacing system is implanted, the physician undertakes a work-up of the patient to determine the pacing energy and sensing thresholds that are sufficient to capture the heart and to distinguish true P-waves and R-waves from muscle artifacts and ambient electrical noise. If LV-PACE and RV-PACE pulses are delivered simultaneously, there may be a current contribution from the highest voltage active electrode delivering the highest voltage pulse to the lower voltage active electrode delivering the lower voltage pulse. The contribution may be sufficient to lower the pacing threshold at the lowest voltage active electrode. Then, at a later time, the programmed mode may be changed by eliminating or lowering the voltage of the highest voltage pacing pulse, and capture may be lost at the lowest voltage active pacing electrode.

As shown in FIG. 5, the IPG circuit 300 of FIG. 3 can be programmed to either only deliver a single RV-PACE or LV-PACE (V-PACE1) or the pair of RV-PACE and LV-PACE pulses (V-PACE1 and V-PACE2) separated by the VP-VP delay timed out by V-V delay timer 366. If delivery of only a single RV-PACE or LV-PACE is programmed as determined in step S200, then it is delivered in step S202.

In accordance with the present invention, the LV-PACE pulse is delivered across the active LV pace electrode 50 and the indifferent ring RV (IND_RV) pace electrode 38 in a trans-ventricular pacing path 60 (shown schematically in FIG. 2) encompassing the bulk of the LV and intraventricular septum separating the pace/sense electrodes. Although the active RV pace electrode 40 could be programmed to be paired as the indifferent electrode with the active LV pace electrode 50 it is generally not desirable to do so since both are of relatively small surface area, and it is usually desirable to provide a relatively large indifferent electrode surface area to function as an anode.

If VP-VP pacing is programmed on in step S200, then V-PACE1 is delivered in step S204 in the programmed RV-LV or LV-RV sequence. Again, the RV-PACE pulse is typically delivered across the active RV tip electrode 40 and one of the available indifferent electrodes that is programmed and selected through the pace/sense electrode selection and control 350 depending upon which are present in the pacing system and the RV pacing vector that is desired as set forth above. And, the LV-PACE pulse is delivered across the active LV pace electrode 50 and the IND_RV pace electrode 38 in the trans-ventricular pacing path 60. The V-PACE1 pacing pulse is delivered at a programmed pulse energy dictated by the programmed voltage and pulse width.

The V-V delay timer 366 is loaded with the programmed VP-VP delay and starts to time out in step S206. If the RV-PACE pulse is V-PACE1, then a programmed VP-VP delay is timed in V-V delay timer 366. The LV-PACE pulse is delivered as V-PACE2 in the LV pacing path 60 between the active LV pace electrode 50 and IND_RV pace electrode 38 in step S210 after time-out of the programmed VP-VP delay in step S208. Conversely, if the LV-PACE pulse is the first to be delivered (V-PACE1) in the pacing path 60, then a programmed VP-VP delay is timed in V-V delay timer 366. The RV-PACE pulse is then delivered as V-PACE2 typically across the active RV pace electrode 40 and the programmed indifferent electrode in step S210 after time-out of the programmed VP-VP delay in step S208.

FIGS. 6A–6B is a flow chart illustrating the steps S112 and S132 of FIG. 4 for delivering ventricular pacing pulses triggered by a ventricular sense event in step S108 during the time-out of an AV delay or in step S124 during time-out of the V-A escape interval. As noted above, the sensing of R-waves in the RV and LV can be accomplished employing several RV-SENSE and LV-SENSE sensing axes or vectors. A bipolar RV-SENSE vector (RV sense electrodes 38 and 40), a unipolar RV-SENSE vector (RV tip sense electrode 40 and IND_CAN electrode 20), and a unipolar LV-SENSE vector (LV sense electrode 50 and IND_CAN electrode 20), and a trans-ventricular, combined RV-SENSE and LV-SENSE vector (RV tip sense electrode 40 and LV sense electrode 50) can be programmed. The selection of the sensing vectors would depend upon heart condition and the selection of the pacing pulse pathways.

The IPG circuit 300 can be separately programmed in one of three triggered pacing modes designated VS/VP, VS/VP-VP or VS-VP triggered modes for each of steps S114 and S132. In the VS/VP triggered pacing mode, a V-PACE1 is delivered without delay upon a RV-EVENT or LV-EVENT to the RV or LV pacing pathway, respectively. In the VS/VP-VP triggered pacing mode, the V-PACE1 is delivered without delay upon a RV-EVENT or LV-EVENT to the selected RV or LV pacing electrode pair, respectively, and a V-PACE2 is delivered to the other of the selected LV or RV pacing electrode pair after the VSNP-VP delay times out. In the VS-VP pacing mode, a RV-EVENT or the LV-EVENT starts time-out of a VS-VP delay, and a single pacing pulse (designated V-PACE2) is delivered to the selected LV or the RV pace electrode pair, respectively, when the VS-VP delay times out.

The TRIG_PACE time window started by a prior V-EVENT or V-PACE must have timed out in step S300 prior to delivery of any triggered ventricular pacing pulses. If it has not timed out, then triggered pacing cannot be delivered in response to a sensed V-EVENT. If the TRIG_PACE window has timed out, it is then restarted in step S302, and the programmed triggered pacing modes are checked in steps S304 and S316.

When IPG circuit 300 is programmed in the VS/VP-VP triggered mode as determined in step S304, the RV-EVENT or LV-EVENT triggers the immediate delivery of a respective RV-PACE or a LV-PACE or a programmed one of the RV-PACE or a LV-PACE across the programmed bipolar or unipolar RV and LV pace electrode pair, respectively, in step S306 as V-PACE1. Under certain circumstances, it is desirable to always deliver V-PACE1 to a designated RV or LV pace electrode pair, regardless of whether a RV-EVENT and LV-EVENT is sensed.

Then, a VS/VP-VP delay is started in step S308 and timed out in step S310. The VS/VP-VP delay is specified as a VP-VP delay when the RV-EVENT is sensed and the RV-PACE is V-PACE1 and the LV-PACE is V-PACE2. The VS/VP-VP delay is specified as a VP-VP delay when the LV-EVENT is sensed and the LV-PACE is V-PACE1 and the RV-PACE is V-PACE2. The LV-PACE or RV-PACE pulse is delivered at the programmed amplitude and pulse width across the programmed LV or RV pace electrode pair in step S210.

In step S314, it is determined whether the VS-VP triggered pacing mode or the VS/VP triggered pacing mode is programmed. When the IPG circuit 300 is programmed to a single heart chamber VS/VP triggered pacing mode, the RV-EVENT or LV-EVENT triggers the immediate delivery of an RV-PACE or an LV-PACE across the programmed bipolar or unipolar RV or LV pace electrode pair, respectively, in step S316.

When the IPG circuit 300 is programmed to the VS-VP triggered pacing mode, an LV-EVENT as determined in step S318 loads the appropriate VS-VP delay in V-V delay timer 366 in step S320 and starts the VS-VP delay time-out in step S322. The RV-PACE is delivered at its time-out in step S322 (also designated V-PACE2). If an RV-EVENT is determined in step S318, then the appropriate VS-VP delay in V-V delay timer 366 in step S326 and the VS-VP delay is timed out in step S328. The LV-PACE (also designated V-PACE2) is delivered at time-out of the VS-VP delay in step S330.

The V-A escape interval is timed out in step S116 following the completion of the ventricular pacing mode of FIGS. 6A–6B for steps S114 and S132. If the V-A escape interval times out, then an RA pace pulse is typically first delivered across the RA pace electrodes 17 and 19 in step S118, and the AV delay timer is restarted in step S100.

In all of steps S306, S312, S316, S324 and S330, the LV-PACE pulse is delivered as V-PACE2 in the LV pacing path 60 between the active LV pace electrode 50 and IND_RV pace electrode 38.

The present invention may also be advantageously implemented in many of the bi-chamber pacing systems described above, e.g. those described in the above-incorporated '324 patent. There is for example no reason it could not be used in conjunction with an Implantable Cardio-Defibrillator (ICD) assuming the ICD also provides the inventive features. For example, FIG. 7 is a comprehensive flow-chart illustrating the operating modes of the IPG circuit 300 of FIG. 3 in a variety of bi-atrial or bi-ventricular pacing modes in accordance with a further embodiment of the invention selectively employing steps of FIGS. 4 through 6A–6B therein. It will be assumed, for example, that the AV synchronous pacing DDD(R) mode is changed to an atrial or ventricular demand, and triggered pacing mode. When FIGS. 4 through 6A–6B are incorporated into steps of FIG. 7 as described below, it will be understood that references to the ventricles (V) in those flow chart steps are appropriate to the bi-ventricular pacing system and method. However, references to the atria (A) can be substituted for the references to the ventricles (V) in those flow chart steps for an understanding of a bi-atrial pacing system and method in accordance with the present invention, where the LA-PACE pulse is delivered across a LA pace electrode pair comprising the active LA pace electrode 64 and the indifferent ring RA (IND_RA) pace electrode 21.

In step S400, the pacing escape interval started in step S418 from a prior R-SENSE or L-SENSE or previously delivered R-PACE or L-PACE (PACE1) is timing out. If the escape interval times out, then the TRIG-PACE window and the post-event time periods, including a conditional refractory period (CRP), the URI and the refractory period (RP) are commenced and timed out in step S402. At the same time, at least a PACE1 pacing pulse is delivered to one of the RHC or LHC in step S404, and the escape interval is restarted in step S418. Step S404 is completed in accordance with the steps of FIG. 5 as described above to either deliver a PACE1 to the selected RHC or LHC pace electrodes or to deliver both PACE1 and PACE2 to both the selected RHC and LHC pace electrodes in a programmed right-to-left or left-to right sequence separated by a programmed P-P delay.

A sense EVENT that is output by any of the RHC or LHC or the trans-chamber sense amplifier during the escape interval in step S402 is characterized as a refractory or non-refractory sense EVENT in step S406. If it is a refractory sense EVENT, then the CRP processing steps are followed as described in the above-referenced 09/439,244 application to determine if it falls within or follows the time-out of the CRP and by how much the post-event time periods are to be continued or extended. In this case, the post-event time periods do not include a PVARP or PVABP, and only include a BP, RP, and URI plus the CRP. The refractory sense EVENT does not trigger delivery of any V-PACE pulses.

If a non-refractory sense EVENT occurs, then the CRP, the URI and the RP are commenced and timed out in step S412. At the same time, it is determined whether a triggered pacing mode is programmed on in step S414. If triggered pacing is off, then the escape interval is restarted in step S418 timed with the non-refractory sense EVENT detected in step S408, and the steps of FIGS. 6A and 6B are followed in step S416.

Triggered pacing proceeds if programmed on in step S416 and if the non-refractory R-EVENT or L-EVENT falls outside the TRIG_PACE window as determined In steps S300 and S302 of FIG. 6A. If triggered pacing is programmed on, then it can be programmed to deliver PACE 1 or PACE2 alone or both PACE1 and PACE2 in the manner prescribed in the remaining steps of FIGS. 6A and 6B. The triggered pacing modes can include delivering PACE1 alone to the RHC or LHC where the sense EVENT was provided or to a programmed one of the right or left heart chamber, regardless of where the depolarization was sensed per step S316.

Or, PACE 1 and PACE2, separated by the programmed or fixed PACE1-PACE2 trigger delay, can be delivered per steps S306–S312 in a programmed sequence. The programmed sequence can comprise delivering PACE1 to the heart chamber where the EVENT was provided or to a programmed one of the RHC or LHC, regardless of where the depolarization was sensed, and then delivering PACE 2 to the other heart chamber at the time-out of the PACE1–PACE2 trigger delay.

Finally, delivery of PACE2 only can be programmed on, as determined in step S314. In that case, steps S314–S330 are followed as described above to deliver PACE2 to the other heart chamber than the heart chamber where the EVENT was provided by the sense amplifier coupled to it after time-out of a SENSE-PACE2 trigger delay.

The preceding specific embodiments are illustrative of the practice of the invention. It is to be understood, therefore, that other expedients known to those of skill in the art or disclosed herein may be employed.

It will be understood that certain of the above-described structures, functions and operations of the pacing systems of the preferred embodiments are not necessary to practice the present invention and are included in the description simply for completeness of an exemplary embodiment or embodiments. It will also be understood that there may be other structures, functions and operations ancillary to the typical operation of such pacing systems that are not disclosed and are not necessary to the practice of the present invention. In addition, it will be understood that specifically described structures, functions and operations set forth in the above-listed, commonly assigned and co-pending patent applications can be practiced in conjunction with the present invention, but they are not essential to its practice.

In the following claims, means-plus-function clauses are intended to cover the structures described herein as performing the recited function and not only structural equivalents but also equivalent structures.

It is therefore to be understood, that within the scope of the appended claims, the invention may be practiced otherwise than as specifically described without actually departing from the spirit and scope of the present invention.

What is claimed is:

1. A method of sensing of spontaneous cardiac depolarizations in right and left heart chambers and delivering right or left heart chamber pacing pulse to the right or left heart chamber for improving the hemodynamic efficiency of a sick heart suffering from conduction delays in conducting depolarizations wherein said method comprises the steps of:

advancing a unipolar pace/sense lead into a left heart chamber blood vessel to situate a left heart chamber active pace/sense electrode of the unipolar pace/sense lead adjacent to the left heart chamber;

advancing a bipolar pace/sense lead into the right heart chamber to locate a right heart chamber active pace/sense electrode and indifferent pace/sense electrode in relation to the right heart chamber;

sensing right heart chamber spontaneous cardiac depolarizations across the right heart chamber active and indifferent pace/sense electrodes and providing a right heart chamber sense event signal;

timing out a pacing interval from a right heart chamber sense event signal or a previously delivered pacing pulse; and upon providing of a right heart chamber sense event signal or upon timing out said pacing escape interval, selectively generating and delivering one of a right heart chamber pacing pulse across said right heart chamber active and indifferent pace/sense electrodes and a left heart chamber pacing pulse along a trans-ventricular pacing path between said left heart chamber active pace/sense electrode and said right heart chamber indifferent pace/sense electrode.

2. The method of claim 1, further comprising the step of:

sensing spontaneous cardiac depolarizations across the right heart chamber and left heart chamber active pace/sense electrodes and providing a left heart chamber sense event signal; and the timing step further comprises the step of:

timing out said pacing interval from a right or left heart chamber sense event signal; and upon a left heart chamber sense event signal, selectively delivering one of a right heart chamber pacing pulse across said right heart chamber active and indifferent pace/sense electrodes and a left heart chamber pacing pulse across said left heart chamber active pace/sense electrode and said right heart chamber indifferent pace/sense electrodes.

3. The method of claim 2, further comprising the steps of:

timing out a triggered pacing delay from the providing of a right heart chamber sense event signal or a left heart chamber sense event signal or the timing out of the pacing interval; and at the time-out of the triggered pacing delay:

selectively generating and delivering the left heart chamber pacing pulse across said left heart chamber active pace/sense electrode and said right heart chamber indifferent pace/sense electrodes when said right heart chamber pacing pulse is delivered across said right heart chamber active and indifferent pace/sense electrodes at the start of the triggered pacing delay; and selectively generating and delivering the right heart chamber pacing pulse across said right heart chamber active pace/sense and indifferent electrodes when said left heart chamber pacing pulse is delivered across said left heart chamber active pace/sense electrode and said indifferent right heart chamber pace/sense electrode at the start of the triggered pacing delay.

4. The method of claim 3, wherein the right heart chamber comprises the right atrium and the left heart chamber comprises the left atrium.

5. The method of claim 3, wherein the right heart chamber comprises the right ventricle and the left heart chamber comprises the left ventricle.

6. The method of claim 1, wherein the right heart chamber comprises the right atrium and the left heart chamber comprises the left atrium.

7. The method of claim 1, wherein the right heart chamber comprises the right ventricle and the left heart chamber comprises the left ventricle.

8. In an implantable medical device having a pacemaker for sensing spontaneous cardiac depolarizations in right and left heart chambers and delivering right or left heart chamber pacing pulse to the right or left heart chamber for improving the hemodynamic efficiency of a sick heart suffering from conduction delays in conducting depolarizations, apparatus comprising:

a unipolar pace/sense lead adapted to situate a left heart chamber active pace/sense electrode of the unipolar pace/sense lead adjacent to the left heart chamber;

a bipolar pace/sense lead adapted to situate a right heart chamber active pace/sense electrode and indifferent pace/sense electrode in relation to the right heart chamber; and a pacing pulse generator comprising:

right heart chamber sensing means for sensing right heart chamber spontaneous cardiac depolarizations across the right heart chamber active and indifferent pace/sense electrodes and providing a right heart chamber sense event signal;

escape interval timing means for timing out a pacing escape interval establishing a pacing rate from a right heart chamber sense event signal;

pacing pulse generating means operable upon providing of a right heart chamber sense event signal or upon timing out said pacing escape interval for selectively generating and delivering one of a right heart chamber pacing pulse across said right heart chamber active and indifferent pace/sense electrodes and a left heart chamber pacing pulse along a trans-ventricular pacing path between said left heart chamber active pace/sense electrode and said right heart chamber indifferent pace/sense electrodes.

9. The pacemaker of claim 8, further comprising:

left heart chamber sensing means for sensing spontaneous cardiac depolarizations across the right heart chamber and left heart chamber active pace/sense electrodes and providing a left heart chamber sense event signal; and wherein:

said escape interval timing means further comprises means for timing out said pacing interval from a right or left heart chamber sense event signal; and said pacing pulse generating means is operable upon provision of a left heart chamber sense event signal for selectively delivering one of a right heart chamber pacing pulse across said right heart chamber active and indifferent pace/sense electrodes and a left heart chamber pacing pulse across said left heart chamber active pace/sense electrode and said right heart chamber indifferent pace/sense electrodes.

10. The pacemaker of claim 9, wherein said pulse generating means further comprises triggered pacing delay timing means for timing out a triggered pacing delay from the providing of a right heart chamber sense event signal or a left heart chamber sense event signal or the timing out of the pacing interval; and wherein:

said pulse generating means is operable at the time out of the triggered pacing delay to selectively generate and deliver the left heart chamber pacing pulse across said left heart chamber active pace/sense electrode and said right heart chamber indifferent pace/sense electrodes when said right heart chamber pacing pulse is delivered across said right heart chamber active and indifferent pace/sense electrodes at the start of the triggered pacing delay and to selectively generate and deliver the right heart chamber pacing pulse across said right heart chamber active pace/sense and indifferent electrodes when said left heart chamber pacing pulse is delivered across said left heart chamber active pace/sense electrode and said indifferent right heart chamber pace/sense electrode at the start of the triggered pacing delay.

11. The pacemaker of claim 10, wherein the right heart chamber comprises the right atrium and the left heart chamber comprises the left atrium.

12. The pacemaker of claim 10, wherein the right heart chamber comprises the right ventricle and the left heart chamber comprises the left ventricle.

13. The pacemaker of claim 8, wherein the right heart chamber comprises the right atrium and the left heart chamber comprises the left atrium.

14. The pacemaker of claim 8, wherein the right heart chamber comprises the right ventricle and the left heart chamber comprises the left ventricle.

15. A method of sensing of spontaneous cardiac depolarizations in right and left ventricles and delivering right or left ventricular pacing pulse to the right or left ventricle for improving the hemodynamic efficiency of a sick heart suffering from conduction delays in conducting spontaneous or evoked depolarizations through the right and left ventricles that compromise cardiac output, wherein said method comprises the steps of:

advancing a unipolar pace/sense lead having only a left ventricular active pace/sense electrode through the coronary sinus of the heart and into a left ventricular blood vessel branching therefrom to situate the left ventricular active pace/sense electrode of the unipolar pace/sense lead adjacent to the left ventricle;

advancing a bipolar pace/sense lead into the right ventricle to locate a right ventricular active pace/sense electrode in the right ventricular apex and an indifferent pace/sense electrode within the right ventricular chamber;

sensing right ventricular spontaneous cardiac depolarizations across the right ventricular active and indifferent pace/sense electrodes and providing a right ventricular sense event signal;

timing out a pacing escape interval from a right ventricular sense event signal;

selectively generating and delivering a right ventricular pacing pulse across said right ventricular active and indifferent pace/sense electrodes at the time-out of said pacing escape interval; and selectively generating and delivering a left ventricular pacing pulse along a transventricular pacing path between said left ventricular active pace/sense electrode and said right ventricular indifferent pace/sense electrodes at the time-out of said pacing escape interval.

16. The method of claim 15, further comprising the step of:

sensing spontaneous cardiac depolarizations across the right ventricular and left ventricular active pace/sense electrodes and providing a left ventricular sense event signal; and the timing step further comprises the step of:

timing out a pacing escape interval establishing a pacing rate from a right or left ventricular sense event signal.

17. A pacemaker for improving the hemodynamic efficiency of a sick heart suffering from conduction delays in conducting spontaneous or evoked depolarizations originating in one of the right or left heart chamber to the other of the left or right heart chamber comprising:

right heart lead means for locating active and indifferent right heart chamber pace/sense electrodes in relation with the right heart chamber;

left heart lead means for locating an active left heart chamber pace/sense electrode in relation with the left heart chamber; and an implantable pulse generator coupled to said right and left heart lead means and comprising:

right heart chamber depolarization sensing means coupled with said right heart chamber lead means for sensing spontaneous cardiac depolarizations originating in the right heart chamber and conducted cardiac depolarizations originating in the left heart chamber due to a spontaneous cardiac depolarization or delivery of a left heart pacing pulse to the left heart chamber and for providing a right heart chamber sense event signal in response to either a sensed spontaneous or conducted cardiac depolarization;

left heart chamber depolarization sensing means coupled with said active left heart chamber pace/sense electrode and one of said active or indifferent right heart chamber pace/sense electrodes for sensing spontaneous cardiac depolarizations originating in the left heart chamber and conducted cardiac depolarizations originating in the right heart chamber due to a spontaneous cardiac depolarization or delivery of a right heart pacing pulse to the right heart chamber and for providing a left heart chamber sense event signal in response to either a sensed spontaneous or conducted cardiac depolarization;

right heart pacing pulse output means coupled with said right heart chamber lead means and selectively responsive to an applied right heart chamber pace trigger signal for generating and delivering a right heart pacing pulse across said active and indifferent right heart chamber pace/sense electrodes to evoke a right heart chamber depolarization;

left heart pacing pulse output means coupled with said right and left heart chamber lead means and selectively responsive to an applied left heart chamber pace trigger signal for generating and delivering a left heart pacing pulse along a crossventricular pacing path between said active left heart chamber pace/sense electrode and said indifferent right heart chamber pace/sense electrode to evoke a left heart chamber depolarization; and escape interval timing means for timing an escape interval establishing a pacing rate and providing one or both of the right and left heart chamber pace trigger signals at the time-out of the escape interval, the escape interval timing means further comprising reset means for restarting the timing of the escape interval upon provision of a pace trigger signal and upon provision of one of the right or left heart chamber sense event signals that is not refractory.

18. A pacemaker for improving the hemodynamic efficiency of a sick heart suffering from conduction delays in conducting spontaneous or evoked depolarizations originating in one of the right or left heart chamber to the other of the left or right heart chamber comprising:

right heart lead means for locating active and indifferent right heart chamber pace/sense electrodes in relation with the right heart chamber;

left heart lead means for locating an active left heart chamber pace/sense electrode in relation with the left heart chamber;

an implantable pulse generator having a housing bearing an indifferent housing pace/sense electrode, said implantable pulse generator further comprising:

right heart chamber depolarization sensing means coupled with said active right heart chamber pace/sense electrode and one of said indifferent right heart electrode or housing pace/sense electrodes for sensing spontaneous cardiac depolarizations originating in the right heart chamber and conducted cardiac depolarizations originating in the left heart chamber due to a spontaneous cardiac depolarization or delivery of a left heart pacing pulse to the left heart chamber and for providing a right heart chamber sense event signal in response to either a sensed spontaneous or conducted cardiac depolarization;

left heart chamber depolarization sensing means coupled with said active left heart chamber pace/sense electrode and one of said active or indifferent right heart or indifferent housing pace/sense electrodes for sensing spontaneous cardiac depolarizations originating in the left heart chamber and conducted cardiac depolarizations originating in the right heart chamber due to a spontaneous cardiac depolarization or delivery of a right heart pacing pulse to the right heart chamber and for providing a left heart chamber sense event signal in response to either a sensed spontaneous or conducted cardiac depolarization;

right heart pacing pulse output means coupled with said right heart chamber lead means and selectively responsive to an applied right heart chamber pace trigger signal for generating and delivering a right heart pacing pulse across said active right heart pace/sense electrode and one of said indifferent right heart or housing pace/sense electrodes to evoke a right heart chamber depolarization;

left heart pacing pulse output means coupled with said right and left heart chamber lead means and selectively responsive to an applied left heart chamber pace trigger signal for generating and delivering a left heart pacing pulse along a transventricular pacing path between said active left heart chamber pace/sense electrode and said indifferent right heart chamber pace/sense electrode to evoke a left heart chamber depolarization; and escape interval timing means for timing an escape interval establishing a pacing rate and providing one or both of the right and left heart chamber pace trigger signals at the time-out of the escape interval, the escape interval timing means further comprising reset means for restarting the timing of the escape interval upon provision of a pace trigger signal and upon provision of one of the right or left heart chamber sense event signals that is not refractory.

19. A pacemaker for improving the hemodynamic efficiency of a sick heart suffering from conduction delays in conducting spontaneous or evoked depolarizations originating in one of the right or left heart chamber to the other of the left or right heart chamber comprising:

right heart lead means for locating active and indifferent right heart chamber pace/sense electrodes in relation with the right heart chamber;

left heart lead means for locating an active left heart chamber pace/sense electrode in relation with the left heart chamber;

an implantable pulse generator having a housing bearing an indifferent housing pace/sense electrode, said implantable pulse generator further comprising:

right heart chamber depolarization sensing means coupled with said active right heart chamber pace/sense electrode and one of said indifferent right heart electrode or housing pace/sense electrodes for sensing spontaneous cardiac depolarizations originating in the right heart chamber and conducted cardiac depolarizations originating in the left heart chamber due to a spontaneous cardiac depolarization or delivery of a left heart pacing pulse to the left heart chamber and for providing a right heart chamber sense event signal in response to either a sensed spontaneous or conducted cardiac depolarization;

left heart chamber depolarization sensing means coupled with said active left heart chamber pace/sense electrode and one of said active or indifferent right heart chamber pace/sense electrodes for sensing spontaneous cardiac depolarizations originating in the left heart chamber and conducted cardiac depolarizations originating in the right heart chamber due to a spontaneous cardiac depolarization or delivery of a right heart pacing pulse to the right heart chamber and for providing a left heart chamber sense event signal in response to either a sensed spontaneous or conducted cardiac depolarization;

right heart pacing pulse output means coupled with said right heart chamber lead means and selectively responsive to an applied right heart chamber pace trigger signal for generating and delivering a right heart pacing pulse across said active right heart chamber pace/sense electrode and one of said indifferent right heart or housing pace/sense electrodes to evoke a right heart chamber depolarization;

left heart pacing pulse output means coupled with said right and left heart chamber lead means and selectively responsive to an applied left heart chamber pace trigger signal for generating and delivering a left heart pacing pulse along a transventricular pacing path between said active left heart chamber and said indifferent right heart chamber pace/sense electrodes to evoke a left heart chamber depolarization; and escape interval timing means for timing an escape interval establishing a pacing rate and providing one or both of the right and left heart chamber pace trigger signals at the time-out of the escape interval, the escape interval timing means further comprising reset means for restarting the timing of the escape interval upon provision of a pace trigger signal and upon provision of one of the right or left heart chamber sense event signals that is not refractory.

20. In a multi-site cardiac pacemaker, a method of selectively sensing spontaneous cardiac depolarizations in the right and left ventricles and delivering pacing pulses to the right and left heart ventricles for improving the hemodynamic efficiency of a sick heart suffering from conduction delays in conducting spontaneous or evoked depolarizations through the right and left heart chambers that compromise cardiac output, wherein said method comprises the steps of:

sensing spontaneous atrial depolarizations and providing atrial sense event signals;

timing out an AV delay from the atrial sense event signals that are characterized as non-refractory;

sensing spontaneous cardiac depolarizations in the right ventricle and providing right ventricular sense event signals;

sensing spontaneous cardiac depolarizations in the left ventricle and providing left ventricular sense event signals;

timing out a V-A escape interval establishing a pacing rate from a selected one of the right and left ventricular sense event signals occurring during the AV delay or the V-A escape interval that is characterized as non-refractory; and at the time-out of the AV delay, delivering a first pacing pulse either as a right ventricular pacing pulse across said active and indifferent right heart chamber pace/sense electrodes to the right ventricle to evoke a right ventricular depolarization or as a left ventricular pacing pulse along a trans-ventricular pacing path between said active left heart chamber pace/sense electrode and said indifferent right heart chamber pace/sense electrode to the left ventricle to evoke a left ventricular depolarization.

21. In a multi-site cardiac pacemaker, a system for selectively sensing spontaneous cardiac depolarizations in the right and left ventricles and delivering pacing pulses to the right and left heart ventricles for improving the hemodynamic efficiency of a sick heart suffering from conduction delays in conducting spontaneous or evoked depolarizations through the right and left heart chambers that compromise cardiac output, wherein said pacemaker further comprises:

a unipolar left ventricular lead adapted to be advanced into a left ventricular blood vessel to situate a left ventricular active pace/sense electrode of the unipolar pace/sense lead adjacent to the left ventricle;

a bipolar right ventricular lead adapted to be advanced into the right ventricle to locate a right ventricular active pace/sense electrode and indifferent pace/sense electrode in relation to the right ventricle;

an atrial lead adapted to be advanced to the atria to locate atrial pace/sense electrodes in relation to the atria; and a pulse generator comprising:

an atrial sense amplifier coupled to the atrial lead for sensing spontaneous atrial depolarizations and providing atrial sense event signals;

an AV delay timer for timing out an AV delay from the atrial sense event signals that are characterized as non-refractory;

a right ventricular sense amplifier coupled to the right ventricular lead for sensing spontaneous cardiac depolarizations in the right ventricle and providing right ventricular sense event signals;

a left ventricular sense amplifier coupled to the right and left ventricular leads for sensing spontaneous cardiac depolarizations in the left ventricle and providing left ventricular sense event signals;

an escape interval timer for timing out a V-A escape interval establishing a pacing rate from a selected one of the right and left ventricular sense event signals occurring during the AV delay or the V-A escape interval that is characterized as non-refractory;

ventricular pacing pulse generating means operable at the time-out of the AV delay for delivering a first pacing pulse either as a right ventricular pacing pulse across the active right ventricular pace/sense electrode and a selected indifferent pacing electrode to evoke a right ventricular depolarization or as a left ventricular pacing pulse along a trans-ventricular pacing path between said active left ventricular pace/sense electrode and said indifferent right ventricular pace/sense electrode to the left ventricle to evoke a left ventricular depolarization; and means responsive to delivery of the first pacing pulse for restarting the timing out of the V-A escape interval.

22. The pacemaker of claim 21, wherein:

said escape interval timing means further comprises means for timing out said pacing interval from a right or left ventricular sense event signal; and said pacing pulse generating means is operable upon provision of a left ventricular sense event signal for selectively delivering one of a right ventricular pacing pulse across said right ventricular active and indifferent pace/sense electrodes and a left ventricular pacing pulse across said left ventricular active pace/sense electrode and said right ventricular indifferent pace/sense electrodes.

23. The pacemaker of claim 22, wherein said pulse generating means further comprises triggered pacing delay timing means for timing out a triggered pacing delay from the providing of a right ventricular sense event signal or a left ventricular sense event signal or the timing out of the pacing interval; and wherein:

said pulse generating means is operable at the time out of the triggered pacing delay to selectively generate and deliver the left ventricular pacing pulse across said left ventricular active pace/sense electrode and said right ventricular indifferent pace/sense electrodes when said right ventricular pacing pulse is delivered across said right ventricular active and indifferent pace/sense electrodes at the start of the triggered pacing delay and to selectively generate and deliver the right ventricular pacing pulse across said right ventricular active pace/sense and indifferent electrodes when said left ventricular pacing pulse is delivered across said left ventricular active pace/sense electrode and said indifferent right ventricular pace/sense electrode at the start of the triggered pacing delay.

* * * * *